US006210948B1

(12) United States Patent
Smit et al.

(10) Patent No.: US 6,210,948 B1
(45) Date of Patent: *Apr. 3, 2001

(54) EXPRESSION AND SECRETION OF HETEROLOGOUS POLYPEPTIDES FROM CAULOBACTER

(75) Inventors: John Smit, Richmond; Wade H. Bingle, Vancouver; John F. Nomellini, Richmond, all of (CA)

(73) Assignee: The University of British Columbia (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/142,648

(22) PCT Filed: Mar. 10, 1997

(86) PCT No.: PCT/CA97/00167

§ 371 Date: Mar. 30, 1999

§ 102(e) Date: Mar. 30, 1999

(87) PCT Pub. No.: WO97/34000

PCT Pub. Date: Sep. 18, 1997

Related U.S. Application Data

(63) Continuation-in-part of application No. 08/614,377, filed on Mar. 12, 1996, now Pat. No. 5,976,864, which is a continuation-in-part of application No. 08/194,290, filed on Feb. 9, 1994, now Pat. No. 5,500,353, which is a continuation-in-part of application No. 07/895,367, filed on Jun. 9, 1992, now abandoned.

(51) Int. Cl.$^7$ ............................... C12N 1/20; C07K 1/00; C07H 21/04

(52) U.S. Cl. ..................... 435/252.3; 530/300; 530/350; 536/23.1; 536/23.7; 536/23.4

(58) Field of Search ........................... 435/252.3, 252.33, 435/320.1, 69.1; 530/350, 300; 536/23.1, 23.4, 23.7

(56) References Cited

U.S. PATENT DOCUMENTS

| 5,143,830 | 9/1992 | Holland et al. ................. 435/69.7 |
| 5,500,549 | 3/1996 | Smit et al. ...................... 435/69.1 |
| 5,976,864 | * 11/1999 | Smit et al. ................... 435/252.3 |

FOREIGN PATENT DOCUMENTS

| 2090549 | 12/1993 | (CA) . |
| 9519371 | 7/1995 | (WO) . |

OTHER PUBLICATIONS

Bingle et al., "Alkaline phosphatase and a cellulase reporter protein are not exported from the cytoplasm when fused . . . ", Canadian Journal of Microbiology, vol. 40, No. 9, Sep. 1994, pp. 777–782.

Gilchrist et al., "Nucleotide sequence of the gene encoding the *Caulobacter crescentus* paracrystalline surface layer protein", Canadian Journal of Microbiology, vol. 38, No. 3, Mar. 1992, pp. 193–202.

Koener et al., "Nucleotide sequence of a cDNA clone carrying the glycoprotein gene of infectious hematopeotic necrosis virus . . . ", Journal of Virology, vol. 61, 1987, pp.1342–1349.

Bingle et al., "Linker mutagenesis of the *Caulobacter crescentus* S–layer protein: toward a definition of a N–terminal anchoring region . . . ", Journal of Bacteriology, vol. 179, No. 3, Feb. 1997, pp. 601–611.

Bingle et al., "The extreme N–terminus of the *Caulobacter crescentus* surface–layer protein directs export of passenger . . . ", Canadian Journal of Microbiology, vol. 42, No. 7, Jul. 1996, pp. 672–684.

Nomellini et al., "insertion of heterologous peptides within the surface–layer protein of *Caulobacter crescentus*", Abstracts of the General Meeting of the American Society for Microbiology, vol. 95, 1995, pg 525.

Smit, John; and, Nina Agabian; "Cloning of the Major Protein of the *Caulobacter crescentus* Periodic Surface Layer: Detection and Characterization of the Cloned Peptide by Protein Expression Assays" (1984) J. Bacteriol. 160, 1137–1145.

John Smit, "Protein Surface Layers of Bacteria", in: *Bacterial Outer Membranes as Model Systems* (1986), John Wiley & Sons, Inc. (M. Inouye, ed.); at p. 344–376.

Fisher, James A.; John Smit; and, Nina Agabian; Transcriptional Analysis of the Major Surface Array Gene of *Caulobacter crescentus*: (1988) J. Bacteriol 170, 4706–4713.

Charbit, Alain; et al; "Versatility of a Vector for Expressing Foreign Polypeptides at the Surface of Gram–Negative Bacteria" (1988) Gene 70, 181–189.

Koener, J.F., et al, "Nucleotide Sequence of a cDNA Clone Carrying the Glycoprotein Gene of Infectious Hematopoietic Necrosis Virus, a Fish Rhabdovirus" (1987) 61 J. Virology, p. 1342–1349, at p. 1345.

Bingle, Wade H.; and, John Smit; "High–Level Expression Vectors for *Caulobacter crescentus* Incorporating the Transcription/Translation Initiation Regions of the Paracrystalline Surface–Layer–Protein Gene" (1990) Plasmid 24, 143–148.

(List continued on next page.)

*Primary Examiner*—Nashaat T. Nashed
(74) *Attorney, Agent, or Firm*—Fish & Richardson P.C.

(57) ABSTRACT

DNA constructs are provided which code for a chimeric protein in which the C-terminal region corresponds to the extreme C-terminal amino acids of a Caulobacter S-layer protein, fused with a heterologous polypeptide. Bacterial cells containing the DNA constructs, or which express the DNA constructs and secrete the resulting protein, are provided. Chimeric proteins including the C-terminal amino acids of a Caulobacter S-layer protein are provided, including proteins which include antigenic epitopes of the Infectious Hematopoietic Necrosis Virus.

23 Claims, 11 Drawing Sheets

OTHER PUBLICATIONS

Gilchrist, A. and Smit, J., "Transformation of Freshwater and Marine Caulobacters by Electroporation" (1991), 173 J. Bacteriology, p. 921–925.

Pugsley, A.P. (1991). Superfamilies of bacterial transport systems with nucleotide binding components. In Prokaryotic Structure and Function: A New Perspective. Edited by S. Mohan, C. Dow, and J.A. Coles. Cambridge University Press, New York. pp. 223–248.

Hayes, L.J.; et al; "Chlamydia trachomatis Major Outer Membrane Protein Epitopes Expressed as Fusions with LamB in an Attenuated aroA Strain of Salmonella typhimurium; Their Application as Potential Immunogens" (1991) J. General Microbiology 137, 1557–1564.

Smit, John; and, James Atwater; "Use of Caulobacters to Separate Toxic Heavy Metals from Wastewater Streams" (Apr., 1991) U.S. Department of Energy Publication.

Smit, J. and Atwater, J., Use of Caulobacters to Separate Toxic Heavy Metals From Wastewater Streams, in: *Proceedings of Waste Stream Management & Utilization Innovative Concepts—An Experimental Technique Exchange* (vol.1) *Mining & Metals Remediation, Wash. D.C. Apr. 25–26, 1991*, U.S. Department of Energy, Pacific Northwest Lab, Richland, Washington; at p. 6.1–6.11.

Federal Grant is First for Manmade Cleanup Bug, in: *Environment Today, vol. 2, Nov./Dec. 1991*.

P. Edwards and J. Smit, "A transducing Bacteriophage for *Caulobacter crescentus* Uses the Paracrystalline Surface Layer Protein as a Receptor" (1991) 173 J. Bacteriology, p. 5568–5572.

W.H. Bingle and J. Smit, "A Method of Tagging Specific–Purpose Linkers with an Antibiotic–Resistance Gene for Linker Mutagenesis Using a Selectable Marker", (1991) 151 BioTechniques, p. 150–152.

Walker, S.G. et al, :Isolation and Comparison of the Paracrystalline Surface Layer Proteins of Freshwater Caulobacters, (1992) 174 J. Bacteriology, p. 1783–1792.

Bingle, W.H., et al, "Caulobacters as Potential Biological Agents for Treatment of Pulp and Paper Effluent: Sequestration of Heavy Metals and Depolymerization of Cellulose", in: *BioforBioqual '92, Vancouver, Canada, Jun. 9–11, 1992*.

Gilchrist, Angus; J.A. Fisher; and, J. Smit; "Nucleotide Sequence Analysis of the Gene Encoding the *Caulobacter crescentus* Paracrystalline Surface Layer Protein" (Mar., 1992) CAN. j. Microbiol 38, 193–202.

Bingle, W.H. et al, "Definition of Form and Function for the S–Layer of *Caulobacter crescentus*" in: *Advances in Bacterial Paracrystalline Surface Layers* (1993) Plenum Press (T.J. Beveridge and S.F. Koval ed.), p.181–197 (see enclosed author's copy insert at p.9–11).

Bingle, W.H., et al, Linker Mutagenesis of the *Caulobacter crescentus* S–Layer Protein:, in: *Advances in Bacterial Paracrystalline Surface Layers* (1993) Plenum Press (T.J. Beveridge and S.F. Koval ed.), p. 293–296.

T.J. Beveridge, et al, "Summary Statements", in: *Advances in Bacterial Paracrystalline Surface Layers* (1993) Plenum Press (T.J. Beveridge and S.F. Koval, ed.), p.323–327; at p.325.

Pugsley, A.P. 1993. The complete general secretory pathway in gram–negative bacteria. Microbiol. Rev. 57: 50–108.

Leong, J.A. 1993. Molecular and biotechnological approaches to fish vaccines. Curr. Opin. Biotech. 4:286–93.

Bingle, W.H., Kurtz, H.D., Jr., et Smit, J. 1993. An "all–purpose" cellulase reporter for gene fusion studies and application to the paracrystalline surface (S)–layer protein of *Caulobacter crescentus*. Can. J. Microbiol. 39 : 70–80.

Bingle, W.H., et Smit, J. 1994. Alkaline phosphatase and a cellulase reporter protein are not exported from the cytoplasm when fused to large N–terminal portions of the *Caulobacter crescentus* surface (S)–layer protein. Can. J. Microbiol 40: 777–782.

Walker, Stephen G. et al.; Characterization of Mutants of *Caulobacter crescentus* Defective in Surface Attachment of the Paracrystalline Surface Layer (1994) J. Bacteriol. vol. 176, No. 20, at 6312–6323.

J. Smit et al; Annual meeting of American Society for Microbiology—Poster Presentation, Washington D.C., May 24, 1995.

* cited by examiner

```
       GCTATTGTCGACGTATGACGTTTGCTCTATAGCCATCGCTGCTCCCATGCGCCGCCACTCGTCGTCGCAGGGGGTGTGGGATTTTTTGGAGACAATCCTC
              -35                              -10                                               S.D.

M  A  Y  T  T  A  Q  L  V  T  A  Y  T  N  A  N  L  G  K  A  P    D  A  A  T  T  L  L  D  A  Y  A  T
  1    ATGGCCTATACGACGGCCCAGTTGGTGACTGCGTACACCAACGCCAACCTCGGCAAGGCGCCTGACGCCGCCACGACGCTGCTCGACGCTACGCGA
  1

Q  T  Q  T  G  L  S  D  A  A  A  L  T  N  T  L  K  L  V  N  S  T  T  A  V  A  I  Q  T  Y  Q  F
 35    CTCAAACCCAGACGGCGGCCTCGGACGCCGCCGCGCTGACGAACACGCTGAAGCTGGTCAACAGCACGACGGCTGTGCCATCCAGACGTACCAGTT
100

F  T  G  V  A  P  S  A  A  G  L  D  F  L  V  D  S  T  T  N  D  L  N  D  A  Y  Y  S  K  F  A
 68    CTTCACCGGCGTTGCCCCGTCGGCCGCCGGTCTCGACTTCCTGGTCGACTCGACCACCAACGACCTGAACGACGCGTACTACTCGAAGTTCGCT
200

Q  E  N  R  F  I  N  F  S  I  N  L  A  T  G  E  A  G  A  G  A  T  A  F  A  A  A  Y  T  G  V  S  Y  A  Q
101    CAGGAAAACCGCTTCATCAACTTCTCGATCAACCTGGCCACGGGCGAGGCCGGCGCCGGCGCCACGGCGTTTGCCGCCGCCTACACGGGCGTTTCGTACGCCC
300

T  V  A  T  A  Y  D  K  I  I  G  N  A  V  A  T  A  A  G  V  D  V  A  A  A  V  A  F  L  S  R  Q  A
135    AGACGGTCGCCACCGCCTATGACAAGATCATCGGCAACGCCGTGGCCACCGCCGCTGGCGTCGACGTCGCGGCCGCGGTGGCTTTCCTGAGCCGCCAGGC
400

N  I  D  Y  L  T  A  F  V  R  A  N  T  P  F  T  A  A  A  D  I  D  L  A  V  K  A  A  L  I  G  T  I
168    CAACATCGACTACCTGACCGCCTTCGTGCGCGCCAACACGCCGTTCACGGCCGCTGCCGACATCGATCTCGCCGTCAAGGCCGCCCTGATCGGCACCATC
500

L  N  A  A  T  V  S  G  I  G  G  Y  A  T  A  A  M  I  N  D  L  S  D  G  A  L  S  T  D  N  A  A
201    CTGAACGCCGCCACGGTGTCCGGCATCGGCGGTTACGCCACCGCCGCGATGATCAACGACCTGTCGGACGGCGCCCTGTCGACGGACAACGCGG
600

G  V  N  L  F  T  A  Y  P  S  S  G  V  S  G  S  T  L  S  L  T  T  G  T  D  T  L  T  G  T  A  N  N
235    CTGGGTGAACCTGTTCACCGCCTATCCGTCGTCGGGCGTGTCGGGTTCGACCCTCTCGCTGACCACCGGCACCGACACCCTGACGGGCACCGCCAACAA
700

D  T  F  V  A  G  E  V  A  G  A  A  T  L  T  V  G  D  T  L  S  G  A  G  T  D  V  L  N  W  V  Q
268    CGACACGTTCGTTGCGGGCGAAGTCGCGGGCGCTGCCACCCTGACCGTCGGCGACACCCTGAGCGGCGCCGGCACCGACGTCCTGAACTGGGTGCAA
800

A  A  V  T  A  L  P  T  G  V  T  I  S  G  I  E  T  M  N  V  T  S  G  A  A  I  T  L  N  T  S  S  G
301    GCTGCTCGCGGTTACGGCTCTCCCGACCGGCGTGACGATCTCGGGCATCGAAACGATGAACGTGACGTCGGGCGCTGCGATCACCCTGAACACGTCTTCGG
900
```

```
335   V T G L T A L N T N T S G A A Q T V T A G A G Q N L T A T T A A Q
1000  GCGTGACGGGTCTGACCGCCCTGAACACCAACAGCGGCGCGGCTCAAACCGTCACCGCCGGCGCTGGCCAGAAACTGACCGCCACGACCGCCGCTCA

368   A N N V A V D G R A N V T V A S T G V T S G T T T V G A N S A A
1100  AGCCGCGAACAACGTCGCCGTGGATGGCCGCGCGAACGTCACCGTCGCCTCGACCGGGGTCACGAGCGGCACCACGACCGTCGGGGCCAACTCGGCCGCT

401   S G T V S V S V A N S S T T T G A I A V T G G T A V T V A Q T A G
1200  TCGGGCACCGTGTCGGTGTCGGTGGCGAACTCGAGCACGACCACCGGCGCTATCGCCGTCACCGGTGTACGGCCGTGACCGTGGCTCAAACGGCCG

435   N A V N T L T Q A D V T V T G N S S T T A V T V T Q T A A A T A
1300  GCAACGCCGTGAACACCCTGACGCAAGCCGACGTGACCGTGACCGGTAACTCCAGCACGACCGCCGTGACGGTCACCCAAACCGCCGCCACCGC

468   G A T V A G R V N G A V T I T D S A A A S A T T A G K I A T V T L
1400  CGGGCGCTACGGTCGCGGTCGCAACGGCGCTGTCACCATCACCGACAGCGCCGCGGCTTCGGCCACGACCGCCGGCAAGATCGCCACGGTCACCCTG

501   G S F G A A T I D S S A L T T V N L S G T G T S L G I G R G A L T A
1500  GGCAGCTTCGGCGCCGCCACCATCGACTCGAGCGCGCTGACCACCGTCAACCTGAGCGGCACGGGCACCTCGCTCGGCATCGGCCGTGGCGCTCTGACCG

535   T P T A N T L T L N V N G L T T T G A I T D S E A A A D D G F T T
1600  CCACGCCGACCGCCAACACCCTGACCCTGAACGTCAATGGTCTGACGACGACCGGCGCGATCACCGACAGCGAAGCCGCTGCTGACGATGGTTCACCAC

568   I N I A G S T A S S T I A S L V A A D A T T L N I S G D A R V T I
1700  CATCAACATCGCTGGTTCGACCGCCTCCTCGACGATCGCCAGCCTGGTGGCCGCAGACGCCACGACCCTGAACATCTCGGGCGACGCTCGCGTCACGATC

601   T S H T A A A L T G I T V T N S V G A T L G A E L A T G L V F T G G
1800  ACCTCGCACACCGCCGCCGCCCTGACCGGCATCACGGTGACCAACAGCGTTGGTGCCACTCTCGGCGCCGAACTGGCCACCGGTCTGGTCTTCACGGGCG

635   A G R D S I L L G A T T K A I V M G A G D D T V T V S A T L G A
1900  GCGCTGGCCGTGACTCGATCCTGCTCGGGGCCACGACCAAGGCGATCGTCATGGGCGCCGGCGACGACACCGTCACCGTCAGCGCCACTCTCGGCGC

668   G G S V N G G D G T D V L V A N V N G S S F S A D P A F G G F E T
2000  TGGTGGTTCGGTCAACGGCGGCGACGGCACCGACGTTCTGGTTGCCAACGTCAACGGTTCGTCAGCGCTGACCCGGCTTCGGCGGCTTCGAAACC

701   L R V G A A A Q G S H N A N G F T A L Q L G A T A G A T T F T N V
2100  CTCCGCGTCGGTGCTGCCGCGCAGGGCTCAAGGCTCGCACAACGCCAACGGCTTCACGGCGCTGCAACTGGGCGCGATAGCAGGGGCGACCACGTTCACCAACG
```

FIG. 6c

```
1/1                                            31/11
GAA TAC AAT TCT GGA GCA GAA ATC CTC TCG TTC CCG AAG TGT GAG GAC AAG ACG ATG GGG
glu tyr asn ser gly ala glu ile leu ser phe pro lys cys glu asp lys thr met gly 61/21                                          91/31
ATG AGG GGA AAC TTG GAT GAC TTT GCC TAT CTA GAC GAT CTG GTG AAG GCC TCT GAG AGC
met arg gly asn leu asp asp phe ala tyr leu asp asp leu val lys ala ser glu ser 121/41                                         151/51
AGA GAG GAA TGT CTT GAG GCG CAC GCC GAG ATA ATA TCA ACA AAC AGT GTG ACT CCA TAC
arg glu glu cys leu glu ala his ala glu ile ile ser thr asn ser val thr pro tyr 181/61                                         211/71
CTC CTA TCC AAG TTC CGA TCT CCA CAT CCC GGA ATA AAT GAC GTC TAC GCT ATG CAC AAA
leu leu ser lys phe arg ser pro his pro gly ile asn asp val tyr ala met his lys 241/81                                         271/91
GGC TCC ATC TAT CAC GGG ATG TGC ATG ACG GTC GCT GTG GAC GAG GTA TCC AAG GAC AGG
gly ser ile tyr his gly met cys met thr val ala val asp glu val ser lys asp arg 301/101                                        331/111
ACG ACG TAC AGG GCC CAT CGC GCT ACC AGC TTC ACG AAA TGG GAA CGA CCC TTT GGG GAT
thr thr tyr arg ala his arg ala thr ser phe thr lys trp glu arg pro phe gly asp 361/121                                        391/131
GAG TGG GAG GGC TTT CAC GGA TTG CAC GGA AAC AAC ACC ACC ATT ATT CCA GAC CTG GAG
glu trp glu gly phe his gly leu his gly asn asn thr thr ile ile pro asp leu glu 421/141                                        451/151
AAA TAC GTC GCC CAG TAC AAG ACG AGC ATG ATG GAA CCG ATG AGC ATC AAA TCC GTA CCC
lys tyr val ala gln tyr lys thr ser met met glu pro met ser ile lys ser val pro 481/161                                        511/171
CAT CCA AGC ATC CTG GCC TTC TAC AAT GAG ACA GAC TTA TCA GGG ATC TCC ATC AGG AAA
his pro ser ile leu ala phe tyr asn glu thr asp leu ser gly ile ser ile arg lys 541/181
TTG GAC TCA TTC
leu asp ser phe
```

FIG. 9

EXPRESSION AND SECRETION OF HETEROLOGOUS POLYPEPTIDES FROM CAULOBACTER

This application is a national stage application of PCT/CA97/00167, filed Mar. 10, 1997, which is a continuation-in-part of U.S. Ser. No. 08/614,377, filed Mar. 12, 1996, now U.S. Pat. No. 5,976,864, which is a continuation-in-part of U.S. Ser. No. 08/194,290, filed Feb. 9, 1994, now U.S. Pat. No. 5,500,353, which is a continuation-in-part of U.S. Ser. No. 07/895,367, filed Jun. 9, 1992, now abandoned.

FIELD OF THE INVENTION

This invention relates to the expression and secretion of heterologous peptides, from Caulobacter wherein the heterologous polypeptide is fused with the surface layer protein (S-layer protein) of the bacterium, or a portion of the S-layer protein.

BACKGROUND OF THE INVENTION

Bacterial surface proteins have been used as carriers for foreign (heterologous) polypeptides (particularly in Salmonella and *E. coli*) for various purposes, including the development of live vaccines. In some instances, the heterologous material is expressed as a fusion product with a surface protein of the bacterium. Generally, the use of such surface proteins as a vehicle for expression and/or presentation of heterologous polypeptides has been limited by the characteristics of a particular surface protein. The lipopolysaccharide layer of a bacterium, which tends to stimulate a strong immune response, covers the integral outer membrane proteins of the organism and potentially affects efficient presentation of a cloned epitope. Where the surface protein is functional (for example, as part of a filamentous portion of a bacterial cell surface) there will be limited opportunities to express a fusion product and still retain the surface protein's function. Generally, the organisms that have been used for these purposes have been chosen because of the advantages presented in respect of the organism's relationship to its host.

Many genera of bacteria assemble layers composed of repetitive, regularly aligned, proteinaceous sub-units on the outer surface of the cell. These layers are essentially two-dimensional paracrystalline arrays, and being the outer molecular layer of the organism, directly interface with the environment. Such layers are commonly known as S-layers and are found on members of every taxonomic group of walled bacteria including: Archaebacteria; Chlamydia; Cyanobacteria; Acinetobacter; Bacillus; Acuaspirillum; Caulobacter; Clostridium; Chromatium. Typically, an S-layer will be composed of an intricate, geometric array of at least one major protein having a repetitive regular structure. In many cases, such as in Caulobacter, the S-layer protein is synthesized by the cell in large quantities and the S-layer completely envelopes the cell and thus appears to be a protective layer.

Caulobacter are natural inhabitants of most soil and freshwater environments and may persist in waste water treatment systems and effluents. The bacteria alternate between a stalked cell that is attached to a surface, and an adhesive motile dispersal cell that searches to find a new surface upon which to stick and convert to a stalked cell. The bacteria attach tenaciously to nearly all surfaces and do so without producing the extracelluar enzymes or polysaccharide "slimes" that are characteristic of most other surface attached bacteria. They have simple requirements for growth. The organism is ubiquitous in the environment and has been isolated from oligotrophic to mesotrophic situations. Caulobacters are known for their ability to tolerate low nutrient level stresses, for example, low phosphate levels. This nutrient can be limiting in many leachate waste streams, especially those with high levels of iron or calcium.

All of the freshwater Caulobacter that produce an S-layer are similar and have S-layers that are substantially the same. Such S-layers appear similar by electron microscopy with the layer being hexagonally arranged in all cases with a similar centre—centre dimension (see: Walker, S. G., et al. (1992). "Isolation and Comparison of the Paracrystalline Surface Layer Proteins of Freshwater Caulobacters" J. Bacteriol. 174: 1783–1792). 16S rRNA sequence analysis of several S-layer producing Caulobacter strains suggest that they group closely (see: Stahl, D. A. et al (1992) "The Phylogeny of Marine and Freshwater Caulobacters Reflects Their Habitat" J. Bacteriol. 174:2193–2198). DNA probing of Southern blots using the S-layer gene from *C. crescentus* CB15 identifies a single band that is consistent with the presence of a cognate gene (see: MacRae, J. D. and, J. Smit. (1991) "Characterization of Caulobacters Isolated from Wastewater Treatment Systems" Applied and Environmental Microbiology 57:751–758). Furthermore, antisera raised against the S-layer protein of *C. crescentus* strain CB15 reacts with S-layer proteins from other Caulobacter (see: Walker, S. G. et al (1992) [supra]). All S-layer proteins isolated from Caulobacter may be substantially purified using the same extraction method (pH extraction) which would not be expected to be a general purpose method for other bacterial membrane or surface associated proteins. All strains appear to have a polysaccharide reactive with antisera reactive against CB15 lipopolysaccharide species which appears to be required for S-layer attachment (see: Walker, S. G. et al (1992) [supra]).

The S-layer elaborated by freshwater isolates of Caulobacter are visibly indistinguishable from the S-layer produced by *Caulobacter crescentus* strains CB2 and CB15.

The S-layer proteins from the latter strains have approximately 100,000 m.w. although sizes of S-layer proteins from other species and strains will vary. The protein has been characterized both structurally and chemically. It is composed of ring-like structures spaced at 22nm intervals arranged in a hexagonal manner on the outer membrane. The S-layer is bound to the bacterial surface and may be removed by low pH treatment or by treatment with a calcium chelator such as EDTA.

The similarity of S-layer proteins in different strains of Caulobacter permits the use of a cloned S-layer protein gene of one Caulobacter strain for retrieval of the corresponding gene in other Caulobacter strains (see: Walker, S. G. et al (1992) [supra]; and, MacRae, J. D. et al (1991) [supra].

Expression, secretion and optionally, presentation, of a heterologous polypeptide as a fusion product with the S-layer protein of Caulobacter provides advantages not previously seen in systems using organisms such as *E. coli* and Salmonella where fusion products of other kinds of surface proteins have been expressed. All known Caulobacter strains are believed to be harmless and are nearly ubiquitous in aquatic environments. In contrast, many Salmonella and *E. coli* strains are pathogens. Consequently, expression and secretion of a heterologous polypeptide using Caulobacter as a vehicle will have the advantage that the expression system will be stable in a variety of outdoor environments and may not present problems associated with the use of a pathogenic organism. Furthermore, Caulobacter are natural biofilm forming species and may be adapted for use in fixed biofilm bioreactors. The quantity of S-layer protein that is synthesized and is secreted by Caulobacter is high, reaching 12% of the cell protein. The unique characteristics of the repetitive, two-dimensional S-layer would also make such bacteria ideal for use as an expression system, or as a presentation surface for heterologous polypeptides. This is desirable in a live vaccine to maximize presentation of the antigen or antigenic epitope. In addition, use of such a presentation surface to achieve maximal exposure of a desired polypeptide to the environment results in such bacteria being particularly suited for use in bioreactors or as carriers for the polypeptide in aqueous or terrestrial outdoor environments.

SUMMARY OF THE INVENTION

This invention pertains to the discovery that the C-terminal region of the Caulobacter S-layer protein is essential for secretion of the S-layer protein. The inventors have determined that the 3' region of the gene which encodes the C-terminal region of the S-layer protein is conserved among different strains of Caulobacter.

This invention provides a method of expressing and presenting to the environment of a Caulobacter, a polypeptide that is heterologous to the S-layer protein of the Caulobacter, which comprises inserting a coding sequence for the heterologous polypeptide in-frame into a S-layer protein gene of Caulobacter, or a portion of said S-layer protein gene, whereby the polypeptide is expressed and secreted by the Caulobacter as a chimeric protein comprising the heterologous protein and all or part of the S-layer protein.

This invention provides a DNA construct for the aforemention chimeric protein, and a bacterium comprising such a DNA construct, wherein the DNA construct encodes all or part of a S-layer protein, and one or more in-frame sequences encoding one or more heterologous proteins.

This invention provides a DNA construct comprising one or more restriction sites for facilitating insertion of DNA into the construct and, DNA encoding at least the 82 C-terminal amino acids of Caulobacter S-layer protein. Preferably, the C-terminal amino acids are or correspond to amino acids 944 or 945–1026 of the RsaA protein of *C. crescentus*.

This invention provides a DNA construct comprising DNA encoding a heterologous polypeptide sequence not present in a Caulobacter S-layer protein upstream from and in-frame with DNA encoding at least the 82 C-terminal amino acids of Caulobacter S-layer protein. Preferably, the C-terminal amino acids are or correspond to amino acids 944 or 945–1026 of the rsaA protein of *C. crescentus*.

This invention also provides a secreted protein obtained from the cell surface or cell medium of a Caulobacter cell expressing the aforementioned DNA constructs wherein the secreted protein comprises the heterologous polypeptide and at least the 82 C-terminal amino acids of a Caulobacter S-layer protein. Preferably, the C-terminal amino acids are or correspond to amino acids 944 or 945–1026 of the RsaA protein of *C. crescentus*.

DESCRIPTION OF THE DRAWINGS

For better understanding of this invention, reference may be made to the preferred embodiments and examples described below, and the accompanying drawings in which:

FIG. 6 (comprising FIGS. 6*a*, *b*, and *c*) shows the complete nucleotide sequence of the *C. crescentus* S-layer (rsaA) gene (SEQ ID NO:6) and the predicted translational product in the single letter amino acid code. The −35 and −10 sites of the promoter region as well as the start of transcription and the Shine-Dalgarno sequence are indicated. Partial amino acid sequences determined by Edman degradation of rsaA protein and of sequenced peptides obtained after cleavage with V8 protease are indicated by contiguous underlining. The putative transcription terminator palindrome is indicated with arrowed lines. The region encoding the glycine-aspartate repeats is indicated by underlined amino acid code letters. This region includes five aspartic acids that may be involved in the binding of calcium ions.

FIG. 9 is the nucleotide coding sequence and corresponding amino acid sequence (SEQ ID NO:9) in respect of the 184 amino acid sequence corresponding to amino acids 270–453 of the IHNV surface glycoprotein described in Example 6.

DESCRIPTION OF THE PREFERRED EMBODIMENTS

Figure 1:
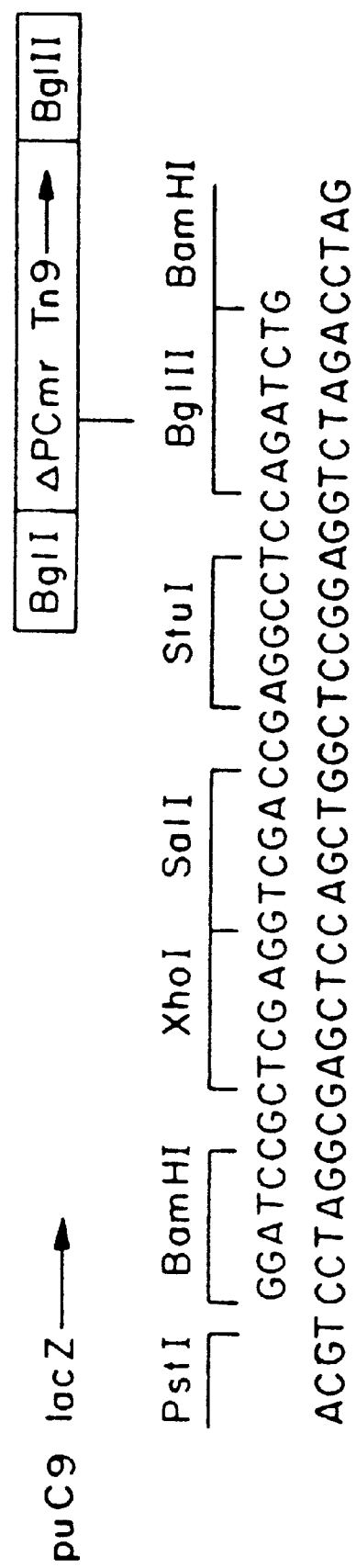
FIG. 1 is the sequence of a Carrier cassette which may be cloned into the PstI/BamHI site of pUC9 to deliver a gene sequence of interest to sites within a *Caulobacter crescentus* S-layer protein (rsaA) gene (SEQ ID NO:1).

The preferred organism for use in this invention is Caulobacter, particularly *C. crescentus*. While similarity of the S-layer gene and S-layer secretion systems permits the use of any S-layer protein producing Caulobacter in this invention, *C. crescentus* strains CB2 and CB15 and variants of those strains which contain homologs of the gene encoding the 1026 amino acid paracrystalline S-layer protein described in: Gilchrist, A. et al. 1992. "Nucleotide Sequence Analysis Of The Gene Encoding the *Caulobacter crescentus* Paracrystalline Surface Layer Protein". Can. J. Microbiol. 38:193–208, are referred to in the examples described below.

Caulobacter strains which either are incapable of forming an S-layer, including those which shed the S-layer protein upon secretion, may be used in this invention. Examples are the variants CB2A and CB15AKSac described in Smit, J., and N. Agabian. 1984. "Cloning of the Major Protein of the *Caulobacter crescentus* Periodic Surface Layer: Detection and Other Characterization of the Cloned Peptide by Protein Expression Assays". J. Bacteriol. 160:1137–1145.; and, Edwards, P., and J. Smit. 1991. "A Transducing Bacteriophage for *Caulobacter crescentus* Uses the Paracrystalline Surface Layer Protein as Receptor". J. Bacteriol. 173, 5568–5572. Examples of shedding strains are CB15Ca5 and CB15Ca10 described in Edwards and Smit (1991) [supra], and the smooth lipopolysaccharide deficient mutants described in Walker, S. G. et al. 1994. "Characterization of Mutants of Caulobacter crescentus Defective in Surface Attachment of the Paracrystalline Surface Layer". J. Bacteriol. 176:6312–6323.

A heterologous polypeptide referred to herein may be any peptide, polypeptide, protein or a part of a protein which is desired to be expressed in Caulobacter and which may be secreted by the bacterium. The heterologous polypeptide includes enzymes and other functional sequences of amino acids as well as ligands, antigens, antigenic epitopes and haptens. The size of the heterologous polypeptide will be selected depending upon whether an intact S-layer is to be produced in the Caulobacter or whether the chimeric protein to be recovered from the bacterial medium as described below. Preferably, the cysteine content of the heterologous polypeptide and the capacity for formation of disulphide bonds within the chimeric protein will be kept to a minimum to minimize disruption of the secretion of the chimeric protein. However, the presence of cysteine residues capable of forming a disulphide bond which are relatively close together, may not affect secretion.

Once a particular bacterium's S-layer protein gene is characterized, this invention may be practised by implementing one or more known methods to insert a selected heterologous coding sequence into all or part of the S-layer protein gene so that both the S-layer protein and the heterologous sequence are transcribed "in-frame". Knowledge of an S-layer protein gene sequence permits one to identify potential sites to install the heterologous genetic material. The repetitive nature of the protein in the S-layer permits multiple copies of a heterologous polypeptide to be presented on the surface of the cell.

The following general procedure lays out courses of action and specifies particular plasmid vectors or constructions that may be used to accomplish fusion of an S-Layer protein with a polypeptide of interest. The following description uses the rsaA (S-layer) gene of *C. crescentus* as an example (see FIG. 6 and SEQ ID NO:6). The latter gene sequence is characterized in Gilchrist, A. et al (1992) [supra].

The general procedure includes detailed steps allowing for the following possibilities:

1) use of a collection of potentially permissive sites in the S-layer gene to install the genetic information for a polypeptide of interest;

2) use of a Carrier cassette for delivering a gene of interest to sites within the S-layer gene (the cassette offers several advantages over direct modification of a gene of interest, in preparation for insertion);

3) creation of a collection of random insertion sites based on a restriction enzyme of choice, if the available collection of potentially permissive sites is for some reason unsuitable; and, 4) preparation of DNA coding for a polypeptide of interest for direct insertion into permissive sites (ie, not using the Carrier cassette) by a method best suited for the particular case (several options are suggested).

Figure 2:
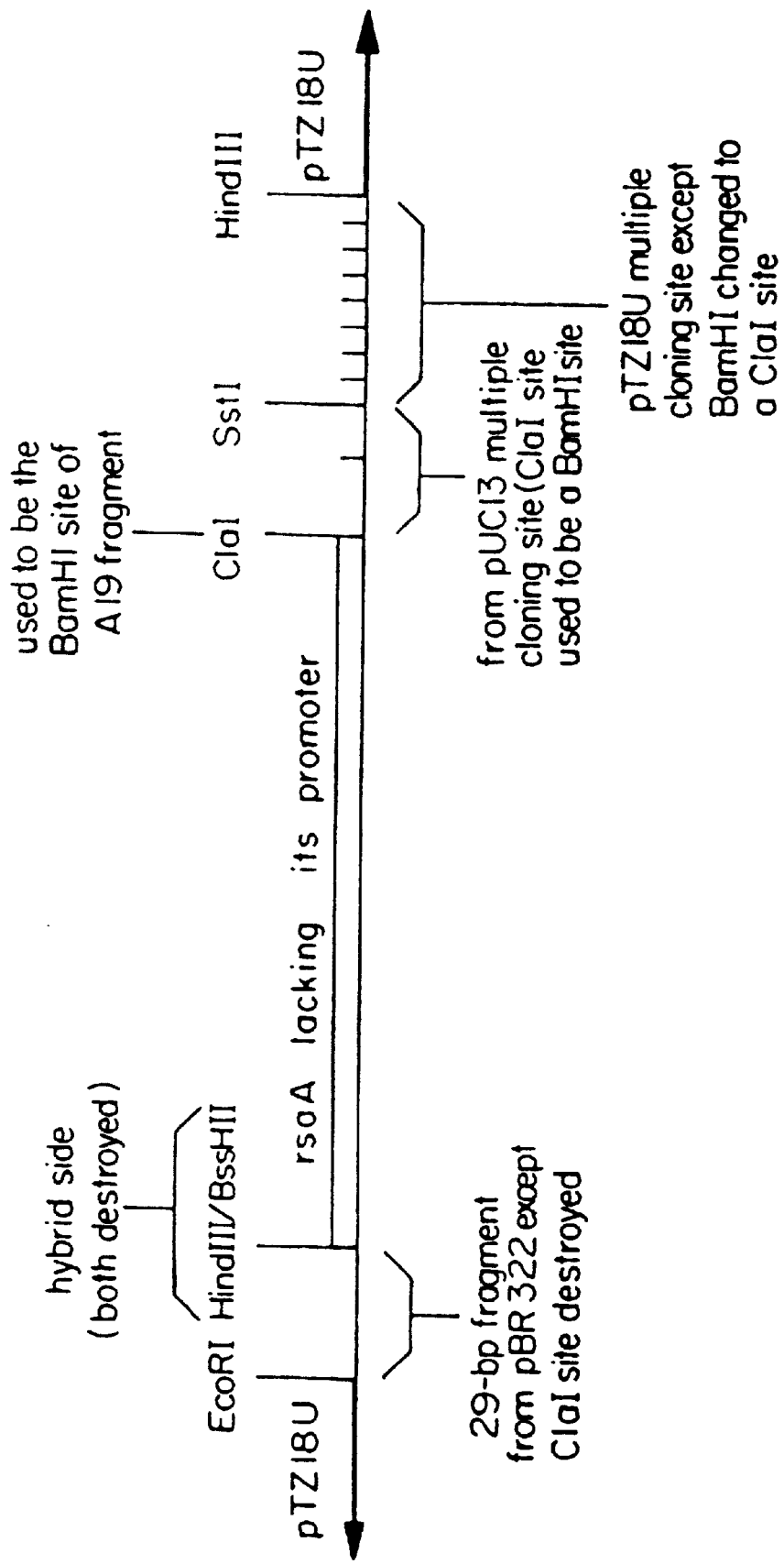
FIG. 2 is a restriction map of a plasmid based promoterless version of the rsaA gene (pTZ18U:rsaAΔP) containing restriction sites and which may be used to accept heterologous DNA of interest.

The general procedure involves the following steps and alternative courses of action. As a first step the practitioner will choose an appropriate region (or specific amino acid position) of the S-layer for insertion of a desired polypeptide. Second, the practitioner will create a unique restriction site (preferably hexameric) in the rsaA (S-layer) gene at a position within the gene encoding that region (or corresponding to a specific amino acid) using either standard linker mutagenesis (regional) or site directed mutagenesis (specific amino acid). The unique restriction site will act as a site for accepting DNA encoding the polypeptide of interest. The plasmid-based promoter-less version of the rsaA gene (pTZ18U:rsaAΔP) shown in FIG. 2 may be used because it contains an appropriate combination of 5' and 3' restriction sites useful for subsequent steps (see: Gilchrist, A. et al (1992) [supra]). The restriction site should not occur in rsaA, its carrier plasmid or the DNA sequence coding for the polypeptide of interest.

If it is unclear which region of the S-layer would be suitable for insertion of a polypeptide of interest, a random linker mutagenesis approach is used to randomly insert a unique linker-encoded restriction site (preferably hexameric) at various positions in the rsaA gene. Sites for insertion of the linker are created using an endonuclease, either of a sequence specific nature (e.g. tetrameric recognition site restriction enzyme) or sequence non-specific nature (e.g. Deoxyribonuclease I [DNase I]). A particularly suitable method is the generalized selectable linker mutagenesis approach based on any desired restriction site of: Bingle, W. H., and J. Smit. 1991 "Linker Mutagenesis Using a Selectable Marker: A Method for Tagging Specific Purpose Linkers With an Antibiotic-Resistance Gene". Biotechniques 10: 150–152. Because endonuclease digestion is carried out under partial digestion conditions, a library of linker insertions at different positions in rsaA is created. Partial digestion with MspI, HinPI and Aci:I can create 150 potential sites for insertion of a Bam HI linker such as:

```
5'-CGACGGATCCGT          (SEQ ID. NO:10).
   TGCCTAGGCAGC-5'
```

If restriction endonucleases are used to create sites for subsequent insertion of a linker encoding a hexameric restriction site, mutagenesis may also be done with a mixture of 3 different linkers incorporating appropriate spacer nucleotides in order to satisfy reading frame considerations at a particular restriction site (only 1 of the 3 linker insertions will be useful for subsequent acceptance of DNA encoding the polypeptide of interest). With DNase I, only one linker is needed, but again only 1 of 3 linker insertions may be useful for accepting DNA encoding the polypeptide of interest depending on the position of the DNase I cleavage with respect to the 3 bases of each amino acid codon.

Figure 3:
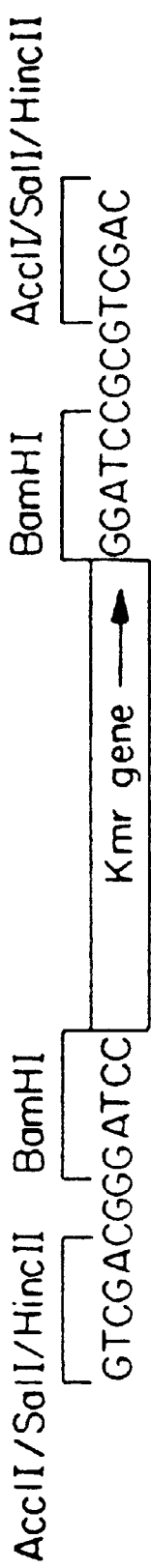
FIG. 3 is the nucleotide sequence of linker BamHI-7165K (SEQ ID NO:2; and SEQ ID NO:3) carried in plasmid pUC9B (pUC7165K), which may be used for mutagenesis at sites created in rsaA by a specific or non-specific endonuclease.
Figure 4:
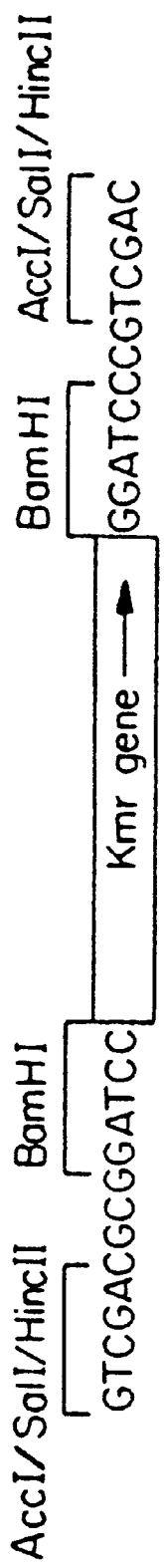
FIG. 4 is the nucleotide sequence a linker BamHI-6571K (SEQ ID NO:4; and SEQ ID NO:5) carried in plasmid pTZ19 (pTZ6571K) which may be used for mutagenesis at sites created in rsaA by a specific or non-specific endonuclease.

Next, a linker tagged with a marker is used to insert DNA of interest at a restriction site. For example, if BamHI sites are appropriate as sites for the introduction of DNA encoding a polypeptide of interest, BamHI linkers tagged with a kanamycin-resistance gene for selectable linker mutagenesis may be used. One such 12-bp linker carried in plasmid pUC1021K was described by Bingle and Smit (1991) [Supra]. Two additional 15-bp linkers (pUC7165K and pTZ6571K) constructed for creating the other 2 possible translation frames within the linker insert itself are described in FIGS. 3 and 4 (SEQ ID NO:2; SEQ ID NO:3; SEQ ID NO:4; and, SEQ ID NO:5). Any one of the above three kanamycin-resistance tagged BamHI linkers is suitable for mutagenesis at sites created in rsaA by DNase I. As outlined above, a mixture of all three linkers is preferably used for mutagenesis at sites created in rsaA by restriction enzyme digestion.

Once a library composed of linker insertions encoding desired hexameric restriction site at different positions in rsaA has been created, the DNA encoding a polypeptide of interest is inserted into the sites en masse (the library of mutated rsaA genes may be manipulated as one unit). The library is digested with the restriction enzyme specific for the newly-introduced linker encoded restriction site and ligated to a DNA fragment encoding the polypeptide of interest and carrying the appropriate complementary cohesive termini. The DNA specifying the polypeptide of interest can be prepared by a number of standard methods, which may include oligonucleotide synthesis of 2 anti-complementary strands, polymerase chain reaction (PCR) procedures, or addition of linkers whose termini are compatible with the introduced sites in rsaA to a suitably modified segment of DNA.

In order to facilitate the rapid recovery of useful rsaA genes carrying newly inserted DNA at BamHI sites encoding the polypeptide of interest, the Carrier oligonucleotide shown in FIG. 1 may be used. The Carrier is designed to accept DNA (including multiple copies and mixtures) prepared by PCR or annealed synthesized oligonucleotides and controls direction of insertion of the foreign segment into a rsaA gene through use of a promoterless drug resistance marker. The DNA of interest is first directionally cloned, if possible, using the XhoI, StuI, or SalI sites or non-directionally cloned using any one of the sites in the same orientation as a promoterless chloramphenicol resistance (CmR) gene. To do this the DNA of interest must be provided with the appropriate termini for cloning and spacer nucleotides for maintaining correct reading frame within the cassette and should not contain a BGlII site. For insertion into the BamHI linker library, the DNA of interest is recovered as a BamHI fragment tagged with a CmR gene. When ligated to the BamHI digested rsaA linker library, only those colonies of the bacterium (eg. *E. coli*) used for the gene modification steps that are recovered will be those carrying insertions of the desired DNA in the correct orientation, since the promoter on the plasmid is 5' to rsaAΔP and the CmR gene. This eliminates screening for DNA introduction and increases the recovery of useful clones by 100% (1 of 3 versus 1 of 6). While still manipulating the library as one unit, the CmR gene is removed using BglII. The carrier oligonucleotide also provides the opportunity to add DNA 5' or 3' to the DNA of interest at SalI, XhoI or StuI sites providing the DNA of interest does not contain any of these sites. This allows some control over spacing between rsaA sequences and the sequence of the DNA of interest.

Next, the rsaA genes carrying the DNA of interest in the correct orientation is excised from the plasmid (eg. from the pTZ18U:rsaAΔP plasmid) and is transferred to a suitable vector providing a promoter recognized by Caulobacter. Such vectors include pWB9 or pWB10 (as described in Bingle, W. H., and J. Smit. 1990). "High Level Plasmid Expression Vectors for *Caulobacter crescentus* Incorporating the Transcription and Transcription-Translation Initiation Regions of the Paracrystalline Surface Layer Protein Gene". Plasmid 24: 143–148) with EcoRI/SstI sites. The DNA of interest should not contain the same restriction sites present in the vector. The latter vectors allow expression of rsaA hybrids in S-layer negative mutants of Caulobacter such as CB15KASac.

Those Caulobacter surviving transfer are examined for chimeric protein secretion, S-layer assembly and presentation of the new polypeptide activity, antigenicity, etc. by methods specific to the needs of the investigator or the capabilities of the inserted sequence. Many of the sites created are "benign" as they have no effect on the functional regions of the protein involved with export, self assembly, etc. However, not every site that results in an absence of functional disruption of the S-layer is best for insertion of new activities. Some sites may not be well exposed on the surface of the organism and other sites may not tolerate insertion of much more DNA than the linker sequence.

By selecting the site of insertion of the heterologous material, it is possible to express heterologous polypeptides of up to about 60 (preferably less than 50) amino acids in a S-layer chimeric protein which will assemble as an S-layer on the cell surface. Single or multiple insertions of smaller polypeptides (eg. 10–20 amino acids) at a wide range of the permissive sites in the S-layer gene will permit S-layer formation. Some sites, as reported herein, are sensitive to even small insertions resulting in the chimeric protein being released into the medium. Release may also be deliberately affected by use of a shedding strain of Caulobacter to express the chimeric protein or by physical removal of the S-layer from whole cells.

Where S-layer formation is not required, this invention permits the expression of quite large polypeptides (eg. about 200 amino acids) as part of the S-layer protein. Expressing a chimeric protein containing a S-layer protein component having substantial deletions, as described below, may increase the size of the heterologous polypeptides that will be expressed and secreted by Caulobacter.

The preceding methods describe insertion of linkers in-frame into an rsaA gene (eg. a promoterless version of the gene). The sites that are introduced allow subsequent insertion of foreign DNA in-frame into the full length rsaA gene. This invention also includes the construction of chimeric S-layer protein genes and the resulting production of chimeric S-layer proteins wherein the S-layer gene component is highly modified by deleting large portions of that gene which reduces the amount of Caulobacter protein present in the secreted chimeric protein.

Generally, large deletions throughout the S-layer gene will result in a chimeric protein that is not capable of forming an S-layer. Attachment of the S-layer to the cell is abolished if about the first 29 N-terminal amino acids of the S-layer protein are deleted. Deletion of the first 776 amino acids from the N-terminal region will still result in a chimeric protein that is secreted from the cell but having a S-layer protein component of only the 250 C-terminal amino acids. It has also been found that only the extreme C-terminal region corresponding to approximately amino acids 945–1026 of RsaA is required for secretion of an S-layer chimeric protein from Caulobacter. Thus the chimeric protein need only have the 82 amino acid C-terminal region of the S-layer protein to be secreted from the cell. Furthermore, use of the C-terminal region corresponding to about amino acids 850–1026 (or more) of RsaA not only permits the cell to transport the chimeric protein outside of the cell, but also promotes spontaneous aggregation of much of the secreted chimeric protein in the cell medium and formation of a macroscopic precipitate that may be collected with a course mesh or sheared to micron-sized particles which may be ideal for vaccine presentation. Yields of up to 250 mg. (dry weight) of protein per liter of cells may be possible.

Sequence analysis of the 3' region of the S-layer genes from different strains of Caulobacter shows that the portion of the gene encoding the C-terminal region of the S-layer protein is highly conserved along with the immediate downstream non-translated and translated region. Sequence analysis of the S-layer genes and downstream regions in CB15 and CB2A (which are readily distinguishable strains) shows identical DNA sequences coding for the last 118 C-terminal amino acids of the S-layer protein and the downstream non-translated region. Sequencing of the next downstream translated gene to amino acid 97 of the gene product shows only a single base pair change between CB15 and CB2A, resulting in a conservative amino acid substitution in the translation product. Conservation of the C-terminal region of Caulobacter S-layer protein and associated coding regions shows that this invention may be carried out using any Caulobacter producing a S-layer protein.

This invention may be practised as shown in the Examples by expression of modified S-layer genes borne on plasmids that are broad host range vectors capable of being expressed in Caulobacter. Such plasmids are readily constructed and introduced to Caulobacter by electroportation. Typically, the plasmid is maintained in the Caulobacter by antibiotic selection. Highly modified rsaA genes with attached heterologous sequences may also be introduced into Caulobacter on a plasmid that is not replicated by Caulobacter. At a low but practicable frequency, homologous recombination of the incoming modified S-layer gene with the chromosome-resident copy of the S-layer gene in the cell will result in a gene rescue or transfer event. In some cases it may be desirable to obtain a stable cell line in which the chimeric S-layer gene is chromosomal. Various protocols for creating chromosomal insertions are set out in the Examples.

Use of the S-layer protein as a vehicle for production of a heterologous polypeptide has several advantages. Firstly, the S-layer protein is synthesized in large quantities and has a generally repetitive sequence. This permits the development of systems for synthesis of a relatively large amount of heterologous material as a fusion product with an S-layer protein (chimeric protein). It may be desirable to retain the chimeric protein as part of the bacterial cell envelope or, the fusion product may be separated from the organism, such as by the method described in: Walker, S. G., et al. 1992. "Isolation and Comparison of the Paracrystalline Surface Layer Proteins of Freshwater Caulobacters". J. Bacteriol. 174:1783–1792. Alternatively, the Caulobacter strain that is used to express the fusion product may be derived from a strain such as CB15Ca5 that sheds its S-layer.

This invention is particularly suited for use in a bioreactor systems. An example would be the use of a modified Caulobacter expressing a polypeptide having activity similar to that of a metallothionein in a bioreactor, to bind toxic metals in sewage, waste water etc. Caulobacters are ideal candidates for fixed-cell bioreactors, the construction of which is well known. An example of such a bioreactor is a rotating biological contactor. Although other bacteria are found in the environment that are capable of binding metals, they often do so by producing copious polysaccharide slimes that quickly plug filtration systems. In some cases, the bacteria are not surface-adherent or the bacteria do not show selectivity towards key toxic metals. By taking advantage of the natural bio-film forming characteristics of Caulobacter, bioreactors may be formed comprising a substrate and a single layer of cells adhered thereon, with the cells distributed at high density. A variety of substrates may be used such as a column of chemically derivatized glass beads or a porous ceramic material such as ceramic foam.

Another advantageous application for this invention is in the production of batch cultures of modified Caulobacter wherein the S-layer protein is a fusion product with an enzyme. For example, such Caulobacter could be grown in wood pulp suspensions at an appropriate juncture of the pulping process in order to provide for enzymatic decomposition of the wood-pulp structure (e.g. with an enzyme having an activity like xylanase or cellulase). Such an application may permit more effective penetration of bleaching agents in the wood-pulp bleaching process thereby reducing the use of chlorine-based bleaching agents.

Examples of enzymes that may be expressed as chimeric S-layer proteins include alkaline phosphatase (eg. by expression of the pho A gene of *E. coli*; see: Hoffman, C. S., and Wright, A. 1985. "Fusions of Secreted Protein to Alkaline Phosphatase: An Approach for Studying Protein Secretion". Proc. Natl. Acad. Sci. U.S.A. 82:5107–5111; Bingle, W. H., et al. 1993."An "All Purpose" Cellulase Reporter for Gene Fusion Studies and Application to the Paracrystalline Surface (S)-Layer Protein of *Caulobacter crescentus*". Can.J. Microbiol.39: 70–80; and Bingle, W. H. and Smit, J. 1994. "Alkaline Phosphatase and a Cellulase Reporter Protein Are Not Exported From the Cytoplasm When Fused to Large N-terminal Portions of the *Caulobacter crescentus* Surface (S)-Layer Protein". Can.J. Microbiol. 40:777–782.) and, cellulase (eg. by expression of the CenA gene of *Cellulomonas fimi*; see: Bingle, W. H. et al. (1993) [supra]; and Bingle, W. H. and Smit, J. (1994) [supra]).

Another advantageous application of this invention is the production of organisms that secrete and optionally present vaccine-candidate epitopes. For example, modified Caulobacter may be readily cultured in outdoor freshwater environments and would be particularly useful in fish vaccines. The two-dimensional crystalline array of the S-protein layer of Caulobacter, which has a geometrically regular, repetitive structure, provides an ideal means for dense packing and presentation of a foreign epitope to an immune system in cases where the epitope is part of an intact S-layer in the bacterial cell surface.

This invention also provides an efficient expression system for polypeptides that may be harvested in large quantities relatively free of contaminants and protein of Caulobacter origin. Expression of a heterologous polypeptide fused with sufficient C-terminal amino acids of the S-layer protein to promote secretion of the heterologous polypeptide results in the accumulation of large quantities of secreted protein in the cell medium. In such cases, the chimeric protein does not have to be released from the cell surface. Furthermore, adjustment of the size of the S-layer protein portion can dictate whether the secreted chimeric protein is soluble or will precipitate in the cell medium. This embodiment may also be useful in cases where the Caulobacter is to express a foreign antigenic component and it is desired to minimize the amount of Caulobacter protein that is associated with the foreign antigen secreted by the Caulobacter.

EXAMPLE 1

Production of Permissive Insertion Sites in *C. crescentus*

Figure 5:
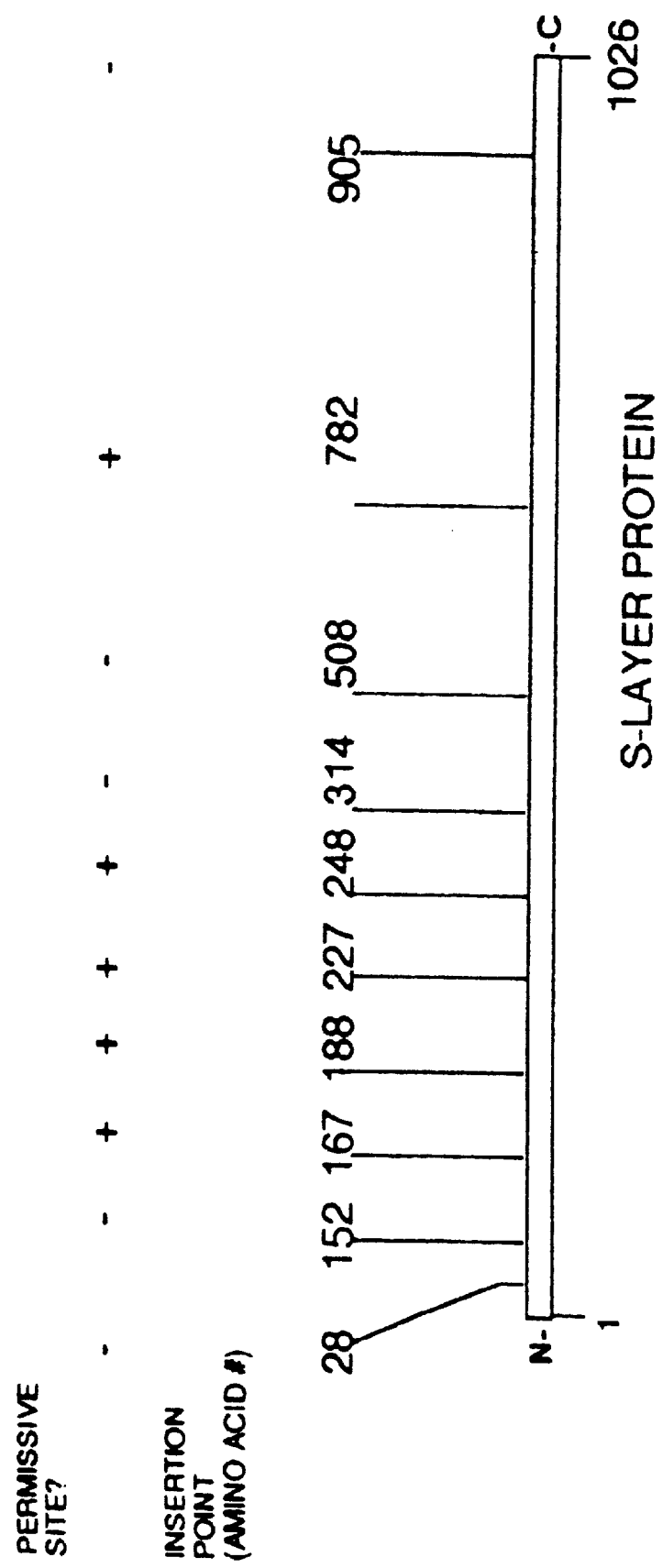
FIG. 5 is a map of insertion events at TaqI sites in the rsaA gene identified by amino acid number of the insertion site in the S-layer protein and scored according to whether the S-layer is produced in the modified organism.

Using the restriction enzyme TaqI, a partial digestion of the rsaA gene in pTZ18U:rsaAΔP produced a group of linearized segments with random TaqI sites cleaved. The linearized segments were modified by use of the tagged linker mutagenesis procedure of Bingle and Smit (1991) [supra], using the 12-bp BamHI linker carried in plasmid pUC102K discussed in the general procedure above. Those products that produced a full-length protein in *E. coli* were ultimately transferred to pWB1 (a minor variation of pWB9 that is replicated by Caulobacter), as described in the general procedure. The resulting construction was introduced into a *C. crescentus* strain. Distinguishable events were retrieved and analyzed for the ability to produce a full-length protein in *C. crescentus* and to produce the crystalline S-layer on their surface and the approximate location of the insertion. Cells were screened for the presence of a S-layer protein of approximately 100 kDa that is extracted from the surface of whole cells by 100 mM HEPES at ph2. The results of this screening together with the approximate positions of five successful events (and subsequently determined exact or specific insertion positions) are illustrated in FIG. 5.

The above-described five positive events represent cases where the 4-amino acid insertion is tolerated with no effect on the S-layer function. The S-layers of the modified Caulobacter were indistinguishable from a wild-type S-layer. Thus, they have a higher potential for tolerating the addition of more foreign peptide material than less characterized sites. By producing 3 versions of the gene of interest, representing each possible reading frame (using standard linker addition technology), one may test each of these sites for suitability in expressing the desired activity. Also, by using restriction enzymes other than TaqI (such as AciI, HinPI or MspI) a larger library of BamHI insertions may be created.

EXAMPLE 2

Insertion of Cadmium Binding Polypeptides into Specific Sites

Figure 6C:
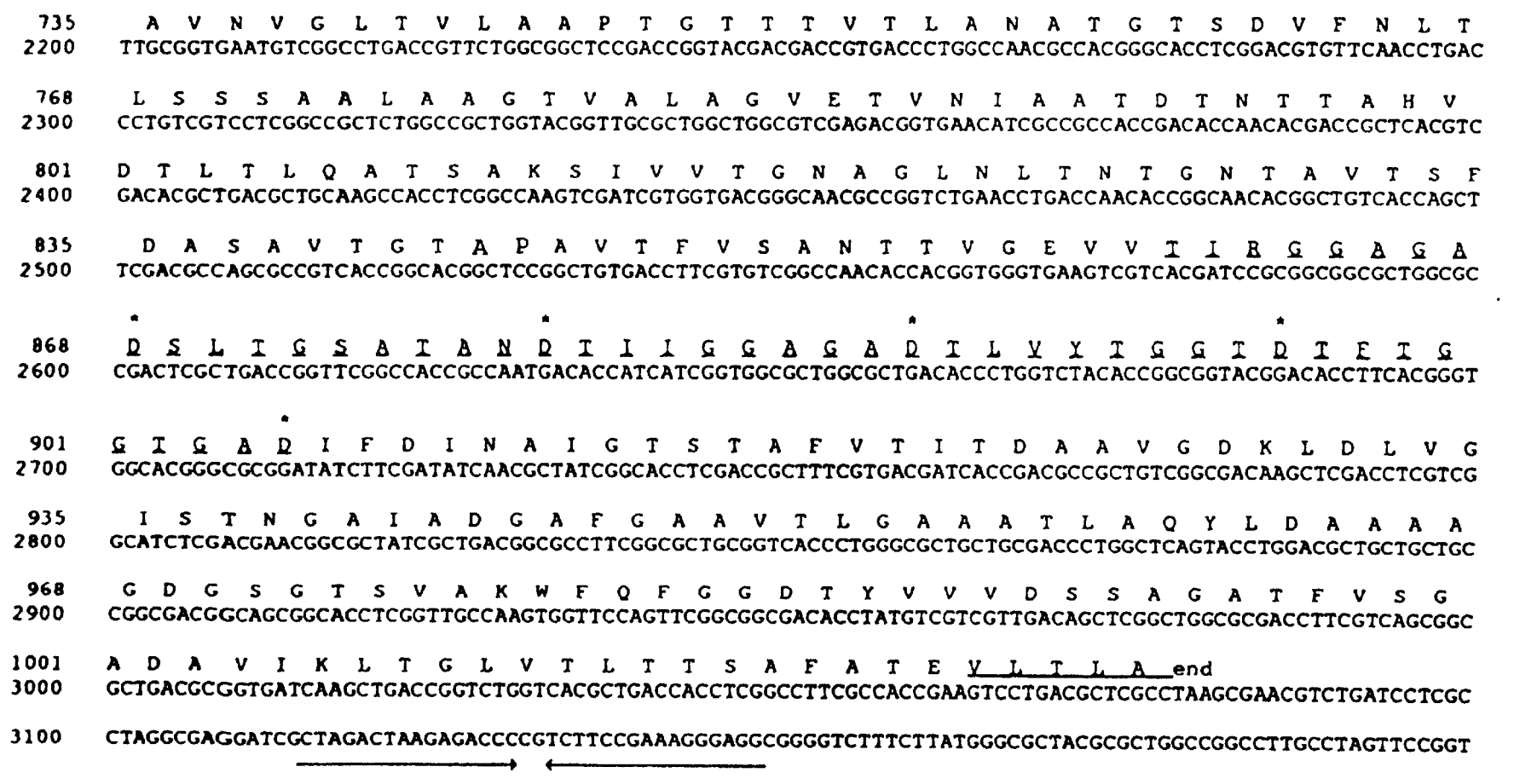

An insertion of the above described 12 bp linker was made at the TaqI site that corresponds to amino acid #188, frame #3 (see FIG. 6; SEQ ID NO:6; and, SEQ ID NO:7). This created a unique BamHI site at that position. Because the precise position of the TaqI site could be assessed from the DNA sequence information available for the rsaA gene, the necessary translation frame was known and thus a single construction of a metallothionein gene was made. This was done by excision of the coding sequence of monkey metallothionein II peptide (60 amino acids comprising 10 cysteine residues and having a molecular weight of about 5000) at known restriction sites and adapting the gene ends with BamHI linkers with appropriate base pair spacers for the needed translation frame.

After insertion into the BamHI site created at position 188, frame 3, several clones were examined by determining whether they could bind elevated levels of cadmium by the assay described below. The assay was necessary because the segment had equal probability of being inserted backwards. One clone that gave positive results was examined by electron microscopy and the presence of a normal S-layer was confirmed. The plasmid in the clone that gave positive results was also examined by DNA sequencing analysis, sequencing across the junction between the position 188 site and the 5' side of the metallothionein gene. The sequence data confirmed correct orientation.

The plasmid-containing clone and relevant control strains were examined for the ability to bind several metals known to be bound by native metallothionein. This was done by growing the strains of bacteria in the presence of the metals at a concentration of 5 ug/ml. After extensive washing of the cells to remove unbound metal, the cells were ashed by treatment at 500° C. and the residue was dissolved in dilute nitric acid and examined for metal content by atomic absorption spectroscopy. The results from one round of data collection is shown in Table 1. In the case of cadmium and copper, an elevated level of bound metal is noted in the metallothionein-expressing strains.

TABLE 1

| | Metal Ion Tested ($\mu$g/metal/OD unit of cells) | | | | |
|---|---|---|---|---|---|
| | Copper | | | | |
| Caulobacter | Trial | 1 | 2 | Cadmium | Zinc |
| CB15 (wild-type,S-layer[+]) | 1.79 | | 1.0 | 0.71 | 4.15 |
| CB15KSAC (S-layer negative strain) | 2.18 | 1.33 | 1.07 | 4.09 | |
| CB15KSAC/p188.3 (contains S-layer with linker insert only) | 2.01 | | 1.30 | 11.1 | 3.66 |
| CB15KSAC/p188.3MT (S-layer with Metallothionein inserted) | 2.79 | | 3.09 | 19.1 | 3.00 |

EXAMPLE 3

Investigation of Other Permissive Sites in rsaA Gene

A library of 240 BamHI linker insertions was created using the procedures of Example 1. of the 240 insertions, 45 target sites in the rsaA gene were made with TaqI. 34 of the latter insertions were discarded because the clones contained deletions of rsaA DNA as well as the linker insertions. The remaining 11 resulted in 5 non-permissive and the 6 permissive sites described in Example 1. The remaining 195 insertions in the library were made using the enzymes HinPI, AciI, and MspI to create target sites as outlined in Example 1. Of the latter 195 insertions, 49 permissive sites were located for a total of 55. Of those sites scored as non-permissive, some may have had deletions of rsaA DNA at the linker insertion site. One BamHI linker insertion at a TaqI site thought to be permissive was later found by nucleotide sequencing to be located outside the rsaA structural gene reducing the total number of permissive sites to 54 from 55.

Figure 7:
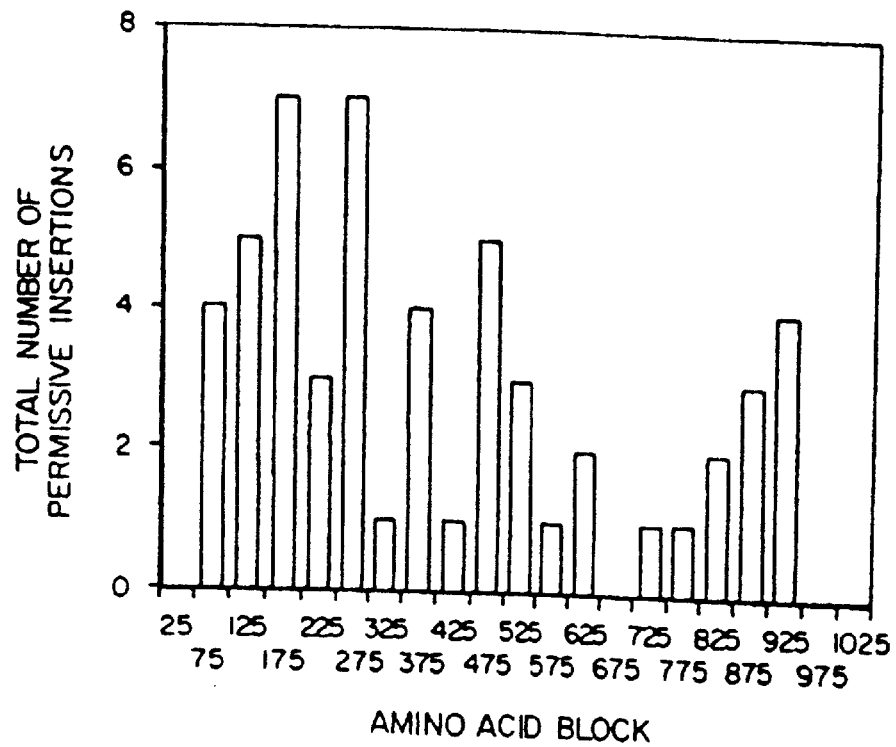
FIG. 7 is a bar graph showing the approximate location by amino acid block of 54 permissive sites in the rsaA gene corresponding to TaqI, HinPI, AciI, and MspI sites described in Example 3.

FIG. 7 illustrates the approximate location by restriction mapping of 54 permissive sites. The results show that sites that will accept 2–4 amino acids while still allowing the protein to be made and assembled into an S-layer are scattered up and down the protein. Furthermore, there is an unexpectedly high proportion of sites at which such insertions do not prevent expression and assembly of the S-layer. The results indicate that approximately 25–50% of in-frame linker insertions will be tolerated by the S-layer protein and the Caulobacter and that diverse regions of the protein will tolerate insertions. Thus, Caulobacter is an ideal candidate for expression of polypeptides fused with the S-layer and the presence of multiple permissive sites extending along the rsaA gene will permit the insertion of a plurality of the same or different peptides into the same RsaA protein molecule and expressed on the surface of a single Caulobacter.

EXAMPLE 4

Further Studies with Cadmium Binding Polypeptides

The results described for Example 3 indicated that it would be possible to insert metallothionein at multiple places in the RsaA protein and thereby enhance the metal binding capacity of such a transformed Caulobacter. However, when the procedures of Example 2 were repeated to insert the metallothionein coding sequence into others of the 54 permissive sites identified in the preceding Example in each case, the transformed Caulobacter did not secrete a chimeric protein and did not synthesize an S-layer. Furthermore, the transformed Caulobacter of Example 2 was stable as long as the transformants were frozen immediately after isolation. When continuously cultured for approximately one week, the transformants deleted the metallothionein portion of the S-layer and the S-layer protein returns to its normal size.

Consideration of the predicted amino acid sequence of the rsaA protein shows that the latter protein lacks cysteine residues whereas metallothionein has a high cysteine content. It thus appeared that for secretion and long term expression of a RsaA chimeric protein, the heterologous polypeptide portions of the chimeric protein should not have high cysteine content and preferably, not be capable of forming multiple disulphide bonds in the chimeric protein in an aerobic environment.

Figure 10:
FIG. 10 is the amino acid sequence of the synthetic cadmium binding peptide referred to in Example 4. The cadmium binding site is shown in the figure.

Following the foregoing procedures, single and multiple copies of DNA encoding the synthetic cadmium binding peptide shown in FIG. 10 (SEQ ID NO:11) was synthesized, inserted at the amino acid 277 site of rsaA using the above described Carrier cassette and was expressed in *C. crescentus*. The peptide has a single cysteine residue. Mild acid extracts of whole cells expressing the modified rsaA gene were subjected to SDS-PAGE for identification of S-layer proteins. The S-layer protein was expressed and secreted when there was from 1 to 3 copies of the cadmium binding peptide present at RsaA amino acid position 277. Insertion of 4 or more copies resulted in a dramatic reduction of S-layer protein released from the whole cells by mild acid treatment to barely detectable levels. Detection by autoradiography of RsaA protein in vivo labelled with 35 S-cysteine and in vitro with 125 I-iodoacetamide confirmed that the cadmium binding peptide was part of the chimeric RsaA protein. This demonstrates that *Caulobacter crescentus* is capable of secretion of a chimeric rsaA protein having a limited cysteine content and a limited capacity for disulphide bond formation within the chimeric protein.

EXAMPLE 5

Expression and Presentation of Antigenic Epitopes on Caulobacter Cell Surface Using the library of the 49 permissive sites other than those made with TaqI described in Example 3, the coding sequence for the 12-amino acid pilus peptide epitope lacking cysteine residues from *Pseudomonas aeruginosa* PAK pilin was inserted at the sites using the procedures described above and employing the Carrier cassette shown in FIG. 1. Positioning of the added DNA between the first Bam HI site and the Bgl II site permitted use of the latter site for making repeated insertions of DNA. The coding sequence for the peptide shown in FIG. 8, including both cysteine residues was also inserted in separate experiments.

Figure 8:
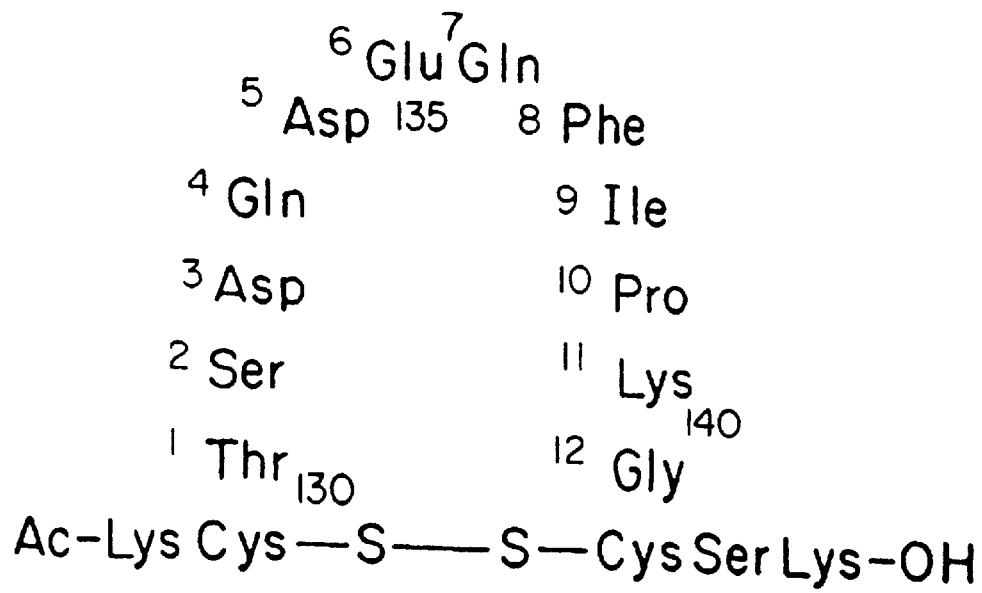
FIG. 8 is a portion of an amino acid sequence (SEQ ID NO: 8) from *P. aeruginosa* PAK pilin in which the 12 amino acid pilus peptide epitope referred to in Example 5 is identified by superscript numerals 1–12.

DNA coding for the peptide shown in FIG. 8 (SEQ ID NO:8) was prepared by oligonucleotide synthesis of two anti-complementary strands. The transformed bacteria were screened for both production and presentation of the epitopes by the transformed Caulobacter by using standard Western immunoblot analysis (see: Burnette, W. N. 1981. "Western Blotting; Electrophoretic Transfer of Protein from Sodium Dodecyl-Polyacrylamide Gels to Unmodified Nitrocellulose and Radiographic Detection Antibody and Radio-iodinated Protein A". Analytical Biochemistry 112:195–203) and by colony immunoblot tests in which the cells were not disrupted (see: Engleberg, N. C., et al. 1984. "Cloning an Expression of *Legionella pneumophilia* Antigens in *Escherichia coli*". Infection and Immunity 44:222–227). Anti-pilus monoclonal antibody obtained from Dr. Irvin, Dept. of Microbiology, University of Alberta (Canada) was used in the immunoblot analyses to detect the presence of the pilus epitope insert. The antibody (called PK99H) was prepared using purified *Pseudomonas aeruginosa* PAK pilin as the antigen and the monoclonal antibody against the 12 amino acid epitope was isolated by standard techniques using BALB/C mice as a source of ascites fluid. Reaction with the antibody in the whole cell colony immunoblot assay shows that the epitope is not only expressed in the transformed Caulobacter but is exposed on the S-layer surface overlying the cell in such a way that the epitope is available to the antibody. When the two cysteine residues of the pilin epitope were incorporated in the chimeric protein, the protein was still expressed and secreted at normal levels. Of the organisms screened, insertions of the pilus epitope at the following sites in the rsaA gene as determined by nucleotide sequencing resulted in a positive reaction with the antibody in the whole cell Colony immunoblot analysis: 69, 277, 353, 450, 485, 467, 551, 574, 622, 690, 723, and 944. The results show that the permissive sites that will accept polypeptides of the size of the pilus epitope are numerous and scattered across the rsaA gene.

Figure 11:
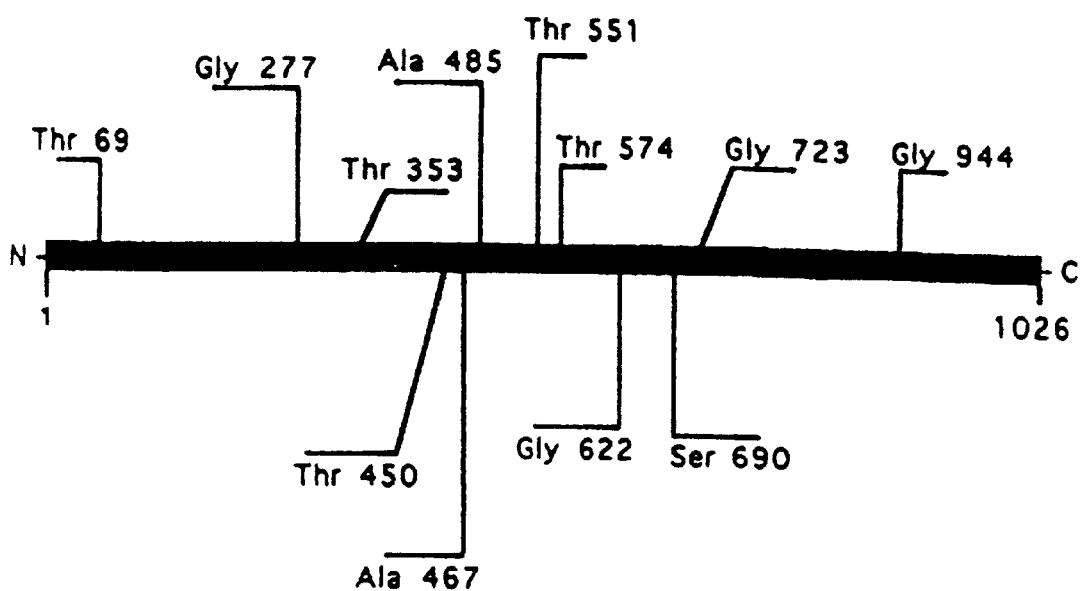
FIG. 11 shows locations of some of the sites in rsaA in which single and multiple copies of the pilus peptide described in Example 5 was expressed and secreted as part of a chimeric rsaA protein.

Further studies with the pilus peptide resulted in successful expression and secretion of RsaA chimeric proteins have single copies of the peptide at the locations shown in FIG. 11. Also, four and seven copies of the 12 amino acid pilus peptide were expressed and secreted as a RsaA chimeric protein when inserted at amino acids 277 and 551 respectively of the RsaA protein. However, insertions of the pilus peptide at amino acids 69, 277, 450, 551 and 622 resulted in a chimeric protein that did not attach to the cell surface and was released into the culture medium.

EXAMPLE 6

Insertion of Large Polypeptides

Bacterial surface proteins from organisms other than Caulobacter described in the prior art are generally not known to accept polypeptides larger than about 60 amino acids within the structure of the surface protein. The procedures of the preceding Example were carried out in order to insert the coding sequence of a 109 amino acid epitope from IHNV virus coat glycoprotein at insertion sites identified in the preceding Example. The IHNV epitope was prepared by PCR and had the portion of the sequence shown in FIG. 9 (SEQ ID NO:9) which is equivalent to amino acid residues 336–444 of the IHNV sequence described in: Koener, J. F. et al. 1987. "Nucleotide Sequence of a cDNA Clone Carrying the Glycoprotein Gene of Infectious Hematopoietic Necrosis Virus, a Fish Rhabdovirus". Journal of Virology 61:1342–1349. Anti-IHNV polyclonal antibody against whole IHNV obtained from Dr. Joann Leong, Dept. of Microbiology, Oregon State University, U.S.A. (see: Xu, L. et al. 1991. "Epitope Mapping and Characterization of the Infectious Hematopoietic Necrosis Virus Glycoprotein, Using Fusion Proteins Synthesized in Escherichia coli". Journal of Virology 65:1611–1615) was used in the immunoblot assays described in the preceding Example to screen for Caulobacter that express and present the IHNV sequence on the surface of the S-layer of the Caulobacter. Reaction in the whole cell colony immunoblot assay was positive in respect of insertions at sites 450 and 551, and negative at a site which was at approximately amino acid 585.

The IHNV insert contains a single cysteine residue and is an extremely large insert for successful expression as a fusion product with a bacterial surface protein.

In further studies, the same 109 amino acid portion of the IHNV glycoprotein was inserted at amino acid 450 of the RsaA protein. The chimeric protein expressed and secreted by *Caulobacter crescentus* and was recovered from the cell culture medium. SDS-PAGE analysis of the recovered proteins showed that some of the chimeric proteins were smaller than the predicted rsaA chimeric protein but still bound anti-IHNV antibody. Analysis of these proteolytic products showed that cleavage of the chimeric protein occurred at an Arg residue encoded by the gene transfer cassette shown in FIG. 1. Thus in some cases, adjustment of the nucleotide sequence at the interface of the polypeptide and rsaA coding sequences may be necessary to prevent expression of an arginine residue.

EXAMPLE 7

Figure 12:
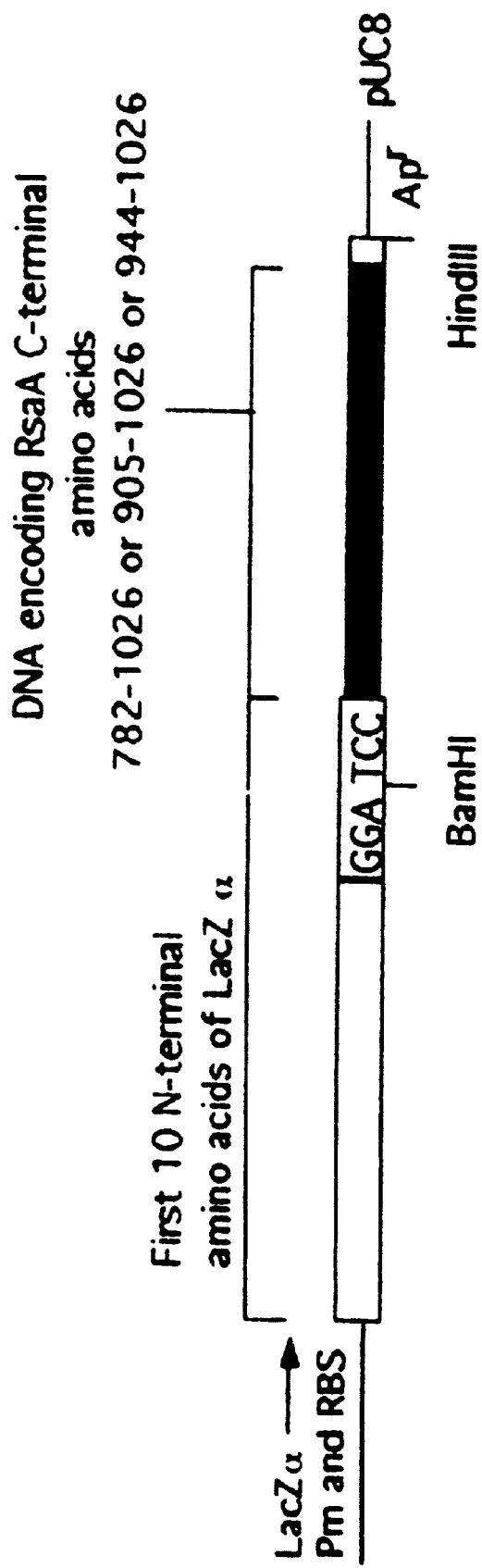
FIG. 12 shows a portion of pUC8 containing various C-terminal fragments of rsaA as described in Example 7.

Methods are described above for the insertion of 12-bp BamHI linker sites into a promoterless version of the rsaA gene. Because linker insertions involve the insertion of 12 bp (i.e. a multiple of three) an in-frame linker insertion resulted in every case. These linker sites are introduced to allow subsequent insertion of DNA encoding foreign peptide/proteins. Expression of such chimeric genes leads to the production of an entire full-length RsaA protein carrying the inserted heterologous amino acid sequence of interest. A number of BamHI site positions were identified above precisely by nucleotide sequencing. Four of the sites in the rsaA gene correspond to amino acid positions 188, 782, 905, 944 in the RsaA protein. For this example, an additional linker insertion was created at amino acid position 95 of the native gene (i.e. this gene carried its own promoter) using the same methodology. All five in-frame BamHI linker insertion sites were inserted in the rsaA so that the nucleotides of the linker DNA were read in the reading frame GGA/TCC (FIG. 12).

Because all BamHI linker nucleotides were read in the same reading frame, the 5' region of one rsaA gene carrying a BamHI linker insertion at one position could be combined with the 3' region of an rsaA gene carrying another of the BamHI linker insertions to create in-frame deletions with a BamHI site at the joint between adjacent regions of rsaA. Using such a method, in-frame deletions of rsaA (ΔAA95–782) and rsaA(ΔAA188–782) were created.

DNA fragments encoding various C-terminal portions of the 1026 amino acid RsaA protein were isolated using the newly inserted BamHI linker sites as the 5'-terminus of the fragment and a HindIII site as the 3' terminus of the fragment. These BamHI fragments were transferred to the BamHI/HindIII sites of pUC8 (J. Vieira, and J. Messing. 1982. "The pUC Plasmids, an M13mp7-Derived System for Insertion Mutagenesis and Sequencing With Synthetic Universal Primers" Gene 19:259–268) creating "rsaA C-terminal Segment Carrier plasmids" (FIG. 12). The insertion into pUC8 also resulted in the creation of an in-frame fusion between the first 10 N-terminal amino acids of LacZα and the various C-terminal fragments (AA782–1026, AA905–1026 or AA944–1026) of RsaA. These LacZα:rsaA fusion proteins can be produced in *C. crescentus* using the lacZα transcription/translation initiation signals when introduced on appropriate plasmid vectors or direct insertion into the chromosome (see: W. H. Bingle, et al. 1993. "An All-Purpose Cellulase Reporter for Gene Fusion Studies and Application to the Paracrystalline Surface (S)—Layer Protein of Caulobacter crescentus." Can. J. Microbiol. 39:70–80).

Both types of constructions (i.e., the deletion versions and the C-terminal only segments) result in the production of proteins that are secreted in Caulobacter strains as highly modified RsaA proteins. The gene segments can also facilitate the secretion of heterologous polypeptides by insertion or fusion of appropriate DNA sequences at the unique BamHI site that exists in each of the constructions. The following describes specific methods for doing so to create chimeric proteins capable of secretion in *C. crescentus*.

A—Creating Fusions of Desired Sequences with C-terminal Portions of rsaA—Method 1

The general process is as follows:
1) Inserting the desired sequence into the Carrier cassette. The following describes the specific manner in which heterologous sequences may be introduced into the Carrier cassette of FIG. 1.
   a) Insertion of a single copy of the desired gene segment.

Depending upon the length of the gene segment, two methods of construction may be used. For segments of up to about 30 amino acids, two oligonucleotides of appropriate sequence are chemically synthesized, annealed by mixing, heating and slow cooling and then ligated into the Carrier cassette. The oligonucleotides will also contain additional base pairs that recreate "sticky ends" of appropriate restriction endonuclease sites at each end of the duplex DNA that results from the annealing process.

For longer segments, PCR is used to amplify a region of a target DNA sequence. Oligonucleotides are synthesized that have sequence complementary to the boundaries of the desired sequence and which contain additional base pairs that recreate a "sticky end" of an appropriate restriction endonuclease site. In the present example oligonucleotides are made to produce products with the appropriate restriction endonuclease site for directional cloning into the Carrier cassette. PCR amplification of the desired sequence is then done by standard methods.

For both methods, the sticky ends prepared must be appropriate for an XhoI site at the 5' terminus of the desired DNA sequence and StuI or SalI sites at the 3' terminus; this places the desired gene segment in the correct orientation within the Carrier cassette. Reading frame continuity is maintained by appropriate design of the oligonucleotides used for the PCR step.

b) Preparation of multiple copies of the desired gene segment.

The Carrier cassette also allows production of multiple insert copies. A BglII site in the cassette is restored after removal of the promoterless antibiotic resistance gene; that site can be used to insert an additional copy of the Carrier/desired sequence insertion, using the terminal BamHI sites, because the "sticky ends" produced by both BamHI and BglII are the same. This "piggy-back" insertion still maintains the correct reading frame throughout the construction. Any number of additional cycles of "piggy-backing" can be done because the BamHI/BglII ligation results in sequence which is no longer a substrate for either enzyme. The result is the production of cassettes of multiple copies of the desired sequence which can be transferred to appropriately modified S-layer protein genes with the same ease as a single copy. An additional feature of this method is that different heterologous sequences can be paired together in this multiple copy cassette with the same ease as multiple copies of the same heterologous sequence.

EXAMPLE 7a

Insertion of an 109 amino acid segment of the IHNV surface glycoprotein to Carrier cassette.

Using the methods described, a PCR product was made that contained the DNA coding for amino acids 336 to 444 (FIG. 9) of the major surface glycoprotein of the Infectious Hematopoietic Necrosis Virus (IHNV), which infects Salmonid fish.

EXAMPLE 7b

Insertion of an 184 amino acid segment of the IHNV surface glycoprotein to Carrier cassette.

Using the methods described a PCR product was made that contained the DNA coding for amino acids 270 to 453 of the IHNV glycoprotein segment shown in FIG. 9.

EXAMPLE 7c

Insertion of single and multiple copies and an epitope of the *Pseudomonas aeruginosa* PAK pilus gene to Carrier cassette.

Oligonucleotides were constructed to code for the pilus epitope described in Example 5, which corresponds to a sequence at the extreme C-terminus of the pilus protein. Using the methods outlined in part A(1)(b) of this Example, 3 tandem copies were prepared.

2) Transfer of Carrier cassette to the rsaA C-terminal Segment Carrier plasmids. The constructions described in examples 7a and 7b above are then transferred to the rsaA C-terminal Segment Carrier plasmids, described above, resulting in an in-frame fusion of: a) a very short section of the betagalactosidase protein (10 amino acids), b) the desired sequence flanked by 2–3 amino acids derived from Carrier cassette sequence and c) the appropriate rsaA C-terminal segment. In some cases, the first codon of the rsaA C-terminal segment is converted to a different codon as a result of the fusion. For example, while the rsaa C-terminal segment may have coded for amino acids 944–1026 of RsaA, the resulting chimeric protein may only have amino acids 945–1026 native to RsaA.

EXAMPLE 7d

Fusion of Carrier/109 AA and 184 IHNV segments to C-terminal rsaA segment AA782–1026.

This was done using the Carrier cassettes described in Examples 7a and 7b above and the AA782–1026 rsaA C-terminal Segment Carrier plasmid described above.

EXAMPLE 7e

Fusion of Carrier/109 AA and 184 AA IHNV segments to C-terminal rsaA segment AA905–1026.

This was done using the Carrier cassettes described in Examples 7a and 7b above and the AA905–1026 rsaA C-terminal Segment Carrier plasmid described above.

EXAMPLE 7f

Fusion of Carrier/109 AA and 184 AA IHNV segments to C-terminal rsaA segment AA944–1026.

This was done using the Carrier cassettes described in Examples 7a and 7b above and the AA944–1026 rsaA C-terminal Segment Carrier plasmid described above.

EXAMPLE 7g

Fusion of Carrier/3x Pilus Epitope segment to C-terminal rsaA segment AA782–1026.

This was done using the Carrier cassettes described in Example 7c above and the AA782–1026 rsaA C-terminal Segment Carrier plasmid described above.

3) Expression of the desired fusion in an appropriate Caulobacter host strain.
    a) Plasmid-based expression.

To create plasmid vectors that can be introduced and maintained in appropriate Caulobacter strains, the entire rsaA C-terminal Segment Carrier plasmids were fused to broad host range vectors pKT215 or pKT210 (see: M. Bagdasarian, et al. 1981. "Specific-Purpose Cloning Vectors. II. Broad-Host-Range, High Copy Number RSF1010-Derived Vectors, and a Host-Vector System for Gene Cloning in Pseudomonas." Gene 16:237–247) using the unique HindIII restriction site present in each plasmid. The resulting plasmid is introduced into Caulobacter by conjugation or electroporation methods and is maintained by appropriate antibiotic selection.

The fusions described in examples 7d–7g were expressed in Caulobacter. In each case expression and secretion of the chimeric S-layer protein was detected by Western immunoblot analysis of electrophoretic gels of the cell culture supermutant employing the monoclonal antibody for each of the polypeptide epitopes. The transporter signal for secretion from Caulobacter must be in the C-terminal region of amino acids 945–1026 of the S-layer protein as all chimeric proteins in the examples were secreted. Precipitation of the chimeric protein occurred with the use of rsaA segment AA782–1026 but not AA944–1026. Recovery of precipitate using AA905–1026 was reduced as compared to AA782–1026.

b) Selection of appropriate Caulobacter host strains.

In nearly all cases the use of a S-layer negative host strain is appropriate. *C. crescentus* strain CB2A and strain CB15aKSac fulfil this requirement. If it is important to ensure that all fusion protein is no longer attached to the cell surface, the use *C. crescentus* strains CB15SCaSKSac or CB15Ca10KSac are appropriate. These strains have additional mutations that result in the loss of the production of a specific species of surface lipopolysaccharide that has been demonstrated to be involved with the surface attachment of native S-layer protein as a 2-dimensional crystalline array (see: Walker S. G. et al 1994. "Characterization of Mutants of *C. crescentus* Defective in Surface Attachment of the Paracrystalline Surface Layer". J. Bacteriol. 176:6312–6323). Most often with the highly modified versions of the S-layer gene, this precaution is not necessary since virtually all regions of the gene that may have a role in the attachment process have been removed.

There are two types of growth media well suited to both propagation of Caulobacter for general purposes, including cloning steps, and also to produce the secreted and aggregated chimeric proteins. Example of the two types are: 1) PYE medium, a peptone and yeast extract based medium described in Walker et al, (1994) [supra], and 2) M6HiGG medium, a defined medium described in: Smit, J., et al 1981. "*Caulobacter crescentus* Pilin: Purification, Chemical Characterization and Amino-Terminal Amino Acid Sequence of a Structural Protein Regulated During Development". J. Biol. Chem. 256, 3092–3097. The latter medium is especially appropriate for preparation of the aggregated chimeric proteins since it permits growth to higher densities (therefore maximizing protein yield) and results in purer aggregated proteins since there are no medium derived proteins to contaminate the chimeric proteins retrieved.

B—Creating Fusions of Desired Sequences with C-terminal Portions of rsaA—Method 2.

Methods other than the use of the Carrier cassette plasmids are possible to create heterologous insertions into deletion versions of a S-layer gene or to create fusions with C-terminal portions of the S-layer protein. PCR may be used although other known methods may also be used. The general procedure is as follows:

1) Use PCR to prepare appropriate segments:
   a) Preparation of amplified segment with appropriate ends is carried out in a manner similar to that described part A(1)(a) above. Oligonucleotides are designed and synthesized such that they will anneal to appropriate regions of the desired heterologous DNA and also contain "sticky ends" of appropriate sequence and frame so that the resulting PCR product can be directed inserted into appropriate modified S-layer genes.
   b) Transfer to appropriate C-terminal rsaA segments is carried out by inserting the PCR products into the C-terminal segments AA782–1026, AA905–1026, or AA944–1026, as described in Examples 7d–7g above. In addition to the BamHI site described, the EcoR1 restriction site could also be used as the 5' terminus of the incoming PCR segment, since this site is also available in the pUC8 vector and not in the S-layer gene, so long as the correct reading frame was maintained when designing the oligonucleotides used to prepare the PCR product.

2) Expression of the desired fusion in an appropriate Caulobacter host strain is carried out using the procedures outlined in part A(3) above.

C—Creating Insertions of Desired Sequences into Versions of a S-layer Gene Having Large Internal In-frame Deletions.

The general process is as follows:

1) Creating appropriate in-frame deletions.

rsaA (ΔAA95–782) and rsaA(ΔAA188–782) were prepared as described above. Because most of the BamH1 linker insertion sites are in the same reading frame with respect to each other, it is possible to combine other pairs of 5' and 3' segments using the same general method, with the same result of maintenance of correct reading frame throughout. These deletion versions must then be tested individually to ensure that S-layer protein is still secreted by the Caulobacter.

2) Insertion of a Gene Segment Carrier cassette containing is the desired sequences: as described at part A(1) above, carried out using the procedure described in part A(2) above.

EXAMPLE 7h

Insertion of the 109 AA IHNV segment into rsaA (ΔAA95–782) and insertion of the 109 AA IHNV segment into rsaA(ΔAA188–782) is carried out as in Examples 7d–7g above. Expression of the desired genetic construction in appropriate *C. crescentus* strains is done using the procedures outlined in part A(3) above.

3) Alternate PCR procedures: can be used to prepare a heterologous segment for direct insertion into the BamHI site with the deletion versions of the rsaA gene. The procedure is essentially the same as described in part B(1) above.

EXAMPLE 8

(Transfer to the native S-layer gene chromosomal site as a single crossover event).

The fusion of the Carrier cassette with appropriate heterologous DNA segments to a C-terminal S-layer protein segment plasmid results in a pUC8-based plasmid that is not maintained in Caulobacter. Selection for the antibiotic marker on the plasmid results in detection of the rescue events. Most commonly these are single crossover homologous recombination events. The result is a direct insertion of the entire plasmid into the chromosome. Thus the resident copy of the S-layer gene remains unchanged as well as the incoming highly modified S-layer gene. In such cases it may be desirable to use Caulobacter strains in which the resident S-layer gene is inactivated in known ways. One example is the use of *C. crescentus* strain CB15AKSac; this strain has an antibiotic resistance gene cassette introduced at a position in the S-layer gene about 25% of the way from the 5' terminus.

EXAMPLE 9

(Transfer to the native S-layer gene chromosomal site as a double crossover event).

In certain cases it may be desirable to completely exchange the resident S-layer gene copy with the incoming highly modified version. One method is the incorporation of a sacB gene cassette (Hynes, M. F., et al. 1989. "Direct Selection for Curing and Deletion of Rhizobium Plasmids Using Transposons Carrying the *Bacillus subtilis* sacB Gene." Gene 78: 111–119) into the pUC8 based plasmids carrying the desired chimeric gene construction. This cassette contains a levansucrase gene from *Bacillus subtilis* that, in the presence of sucrose, is thought to result in the production of a sugar polymer that is toxic to most bacteria when expressed inside the cell. One first selects for the single crossover event as described in Example 8. Subsequent growth on sucrose-containing medium results in the death of all cells except those that lose the offending sacB gene by homologous recombination within the 2 adjacent gene copies. Two events are possible; restoration of the resident copy of the S-layer gene or replacement of the resident copy with the incoming modified gene (the latter is the desired event). A screen with insertion DNA as probe or antibody specific to the heterologous gene product identifies successful gene replacement events. The method requires that the S-layer gene sequence or native sequence immediately adjacent to the S-layer gene be on both sides of the heterologous sequence (ie, Carrier cassette sequence plus heterologous DNA) and in the present case is best suited for the deletion versions of the S-layer gene.

Other methods are available for the delivery of genes to the chromosome of a Caulobacter. Methods involving the use of the transposons Tn5 and Tn7 as a means of delivery of genes to random chromosome locations are available (see: Barry, G. F. 1988 "A Broad-Host-Range Shuttle System for Gene Insertion into the Chromosomes of Gram-Negative Bacteria." Gene 71:75–84.). The use of the xylose utilization operon as a target for chromosome insertion have also been described. This method involves the incorporation of a portion that operon into the pUC8 based plasmid constructions described above. This allows homologous recombination within the xylose operon as a means of plasmid rescue. Loss of the ability to use xylose as a nutrition source is used as the means of confirming the rescue event.

This invention now being described, it will be apparent to one of ordinary skill in the art that changes and modifications can be made thereto without departing from the spirit or scope of the appended claims.

We claim:

1. A nucleic acid comprising:
   a nucleotide sequence encoding a polypeptide consisting of a part of a *Caulobacter crescentus* S-layer protein, the part comprising at least the 82 C-terminal amino acids of the S-layer protein and does not contain amino acids 1–29 of the S-layer protein; and
   one or more restriction sites adjacent to or within the nucleotide sequence.

2. A nucleic acid comprising a sequence encoding a fusion polypeptide, the fusion polypeptide consisting of:
   a part of a *Caulobacter crescentus* S-layer protein, the part comprising at least the 82 C-terminal amino acids of the S-layer protein and does not contain amino acids 1–29 of the S-layer protein; and an amino acid sequence heterologous to the S-layer protein and adjacent to or within the part.

3. The nucleic acid of claim 1, wherein the part comprises amino acids corresponding to about amino acids 945–1026 of SEQ ID NO:7.

4. The nucleic acid of claim 2, wherein the part comprises amino acids corresponding to about amino acids 945–1026 of SEQ ID NO:7.

5. The nucleic acid of claim 1, wherein the part comprises amino acids corresponding to about amino acids 850–1026 of SEQ ID NO:7.

6. The nucleic acid of claim 2, wherein the part comprises amino acids corresponding to about amino acids 850–1026 of SEQ ID NO:7.

7. The nucleic acid of claim 1, wherein the part comprises amino acids corresponding to about amino acids 782–1026 of SEQ ID NO:7.

8. The nucleic acid of claim 2, wherein the part comprises amino acids corresponding to about amino acids 782–1026 of SEQ ID NO:7.

9. The nucleic acid of claim 2, wherein the amino acid sequence heterologous to the S-layer protein comprises one or more polypeptides of up to 200 amino acids in length.

10. A bacterial cell comprising the nucleic acid of claim 2.

11. The cell of claim 10, wherein the cell is a member of the genus Caulobacter.

12. The cell of claim 11, wherein the nucleic acid further comprises a promoter operably linked to the sequence encoding the fusion polypeptide, and the fusion polypeptide is expressed in the cell and secreted from the cell.

13. The cell of claim 12, wherein the cell forms a S-layer comprising the fusion polypeptide on a surface of the cell.

14. The cell of claim 10, wherein the amino acid sequence heterologous to the S-layer protein comprises one or more polypeptides of up to 60 amino acids in length.

15. A bacterial cell comprising the nucleic acid of claim 4.

16. A bacterial cell comprising the nucleic acid of claim 6.

17. A bacterial cell comprising the nucleic acid of claim 8.

18. A bacterial cell comprising the nucleic acid of claim 9.

19. A fusion polypeptide obtained from a cell surface or cell medium of a culture comprising the cell of claim 12, wherein the fusion polypeptide consists of:

a part of a *Caulobacter crescentus* S-layer protein, the part comprising at least the 82 C-terminal amino acids of the S-layer protein and does not contain amino acids 1–29 of the S-aver protein; and an amino acid sequence heterologous to the S-layer protein and adjacent to or within the part, wherein the amino acid sequence comprises one or more polypeptides of up to about 200 amino acids in length.

20. The fusion polypeptide of claim 19, wherein the amino acid sequence comprises one or more polypeptides of up to about 60 amino acids in length.

21. The fusion polypeptide of claim 19, wherein the part comprises amino acids corresponding to about amino acids 945–1026 of SEQ ID NO:7.

22. The fusion polypeptide of claim 21, wherein the part comprises amino acids corresponding to about amino acids 782–944 of SEQ ID NO:7.

23. The fusion polypeptide of claim 19, wherein the amino acid sequence comprises one or more copies of all or part of SEQ ID NO:9.

* * * * *

SEQUENCE LISTING

```
<160> NUMBER OF SEQ ID NOS:  12

<210> SEQ ID NO 1
<211> LENGTH: 44
<212> TYPE: DNA
<213> ORGANISM: Artificial Sequence
<220> FEATURE:
<223> OTHER INFORMATION: Synthetically generated cloning site

<400> SEQUENCE: 1
acgtcctagg cgagctccag ctggctccgg aggtctagac ctag            44

<210> SEQ ID NO 2
<211> LENGTH: 13
<212> TYPE: DNA
<213> ORGANISM: Artificial Sequence
<220> FEATURE:
<223> OTHER INFORMATION: Synthetically generated linker

<400> SEQUENCE: 2
gtcgacggga tcc                                              13

<210> SEQ ID NO 3
<211> LENGTH: 14
<212> TYPE: DNA
<213> ORGANISM: Artificial Sequence
<220> FEATURE:
<223> OTHER INFORMATION: Synthetically generated linker

<400> SEQUENCE: 3
ggatccgcgt cgac                                             14

<210> SEQ ID NO 4
<211> LENGTH: 14
<212> TYPE: DNA
<213> ORGANISM: Artificial Sequence
<220> FEATURE:
<223> OTHER INFORMATION: Synthetically generated linker

<400> SEQUENCE: 4
gtcgacgcgg atcc                                             14

<210> SEQ ID NO 5
<211> LENGTH: 13
<212> TYPE: DNA
<213> ORGANISM: Artificial Sequence
<220> FEATURE:
<223> OTHER INFORMATION: Synthetically generated linker

<400> SEQUENCE: 5
ggatcccgtc gac                                              13

<210> SEQ ID NO 6
<211> LENGTH: 3300
<212> TYPE: DNA
```

-continued

<213> ORGANISM: Caulobacter crescentus
<220> FEATURE:
<221> NAME/KEY: CDS
<222> LOCATION: (101)...(3178)

<400> SEQUENCE: 6

```
gctattgtcg acgtatgacg tttgctctat agccatcgct gctcccatgc gcgccactcg      60 gtcgcaggg gtgtgggatt ttttttggga gacaatcctc atg gcc tat acg acg        115
                                            Met Ala Tyr Thr Thr
                                              1               5 gcc cag ttg gtg act gcg tac acc aac gcc aac ctc ggc aag gcg cct       163
Ala Gln Leu Val Thr Ala Tyr Thr Asn Ala Asn Leu Gly Lys Ala Pro
             10                  15                  20 gac gcc gcc acc acg ctg acg ctc gac gcg tac gcg act caa acc cag       211
Asp Ala Ala Thr Thr Leu Thr Leu Asp Ala Tyr Ala Thr Gln Thr Gln
         25                  30                  35 acg ggc ggc ctc tcg gac gcc gct gcg ctg acc aac acc ctg aag ctg       259
Thr Gly Gly Leu Ser Asp Ala Ala Ala Leu Thr Asn Thr Leu Lys Leu
     40                  45                  50 gtc aac agc acg acg gct gtt gcc atc cag acc tac cag ttc ttc acc       307
Val Asn Ser Thr Thr Ala Val Ala Ile Gln Thr Tyr Gln Phe Phe Thr
 55                  60                  65 ggc gtt gcc ccg tcg gcc gct ggt ctc gac ttc ctg gtc gac tcg acc       355
Gly Val Ala Pro Ser Ala Ala Gly Leu Asp Phe Leu Val Asp Ser Thr
 70                  75                  80                  85 acc aac acc aac gac ctg aac gac gcg tac tac tcg aag ttc gct cag       403
Thr Asn Thr Asn Asp Leu Asn Asp Ala Tyr Tyr Ser Lys Phe Ala Gln
                 90                  95                 100 gaa aac cgc ttc atc aac ttc tcg atc aac ctg gcc acg ggc gcc ggc       451
Glu Asn Arg Phe Ile Asn Phe Ser Ile Asn Leu Ala Thr Gly Ala Gly
            105                 110                 115 gcc ggc gcg acg gct ttc gcc gcc gcc tac acg ggc gtt tcg tac gcc       499
Ala Gly Ala Thr Ala Phe Ala Ala Ala Tyr Thr Gly Val Ser Tyr Ala
        120                 125                 130 cag acg gtc gcc acc gcc tat gac aag atc atc ggc aac gcc gtc gcg       547
Gln Thr Val Ala Thr Ala Tyr Asp Lys Ile Ile Gly Asn Ala Val Ala
        135                 140                 145 acc gcc gct ggc gtc gac gtc gcg gcc gcc gtg gct ttc ctg agc cgc       595
Thr Ala Ala Gly Val Asp Val Ala Ala Ala Val Ala Phe Leu Ser Arg
150                 155                 160                 165 cag gcc aac atc gac tac ctg acc gcc ttc gtg cgc gcc aac acg ccg       643
Gln Ala Asn Ile Asp Tyr Leu Thr Ala Phe Val Arg Ala Asn Thr Pro
                170                 175                 180 ttc acg gcc gct gcc gac atc gat ctg gcc gtc aag gcc gcc ctg atc       691
Phe Thr Ala Ala Ala Asp Ile Asp Leu Ala Val Lys Ala Ala Leu Ile
            185                 190                 195 ggc acc atc ctg aac gcc gcc acg gtg tcg ggc atc ggt ggt tac gcg       739
Gly Thr Ile Leu Asn Ala Ala Thr Val Ser Gly Ile Gly Gly Tyr Ala
        200                 205                 210 acc gcc acg gcc gcg atg atc aac gac ctg tcg gac ggc gcc ctg tcg       787
Thr Ala Thr Ala Ala Met Ile Asn Asp Leu Ser Asp Gly Ala Leu Ser
        215                 220                 225 acc gac aac gcg gct ggc gtg aac ctg ttc acc gcc tat ccg tcg tcg       835
Thr Asp Asn Ala Ala Gly Val Asn Leu Phe Thr Ala Tyr Pro Ser Ser
230                 235                 240                 245 ggc gtg tcg ggt tcg acc ctc tcg ctg acc acc ggc acc gac acc ctg       883
Gly Val Ser Gly Ser Thr Leu Ser Leu Thr Thr Gly Thr Asp Thr Leu
                250                 255                 260 acg ggc acc gcc aac aac gac acg ttc gtt gcg ggt gaa gtc gcc ggc       931
Thr Gly Thr Ala Asn Asn Asp Thr Phe Val Ala Gly Glu Val Ala Gly
```

-continued

```
                 265                 270                 275
gct gcg acc ctg acc gtt ggc gac acc ctg agc ggc ggt gct ggc acc      979
Ala Ala Thr Leu Thr Val Gly Asp Thr Leu Ser Gly Gly Ala Gly Thr
        280                 285                 290 gac gtc ctg aac tgg gtg caa gct gct gcg gtt acg gct ctg ccg acc     1027
Asp Val Leu Asn Trp Val Gln Ala Ala Ala Val Thr Ala Leu Pro Thr
    295                 300                 305 ggc gtg acg atc tcg ggc atc gaa acg atg aac gtg acg tcg ggc gct     1075
Gly Val Thr Ile Ser Gly Ile Glu Thr Met Asn Val Thr Ser Gly Ala
310                 315                 320                 325 gcg atc acc ctg aac acg tct tcg ggc gtg acg ggt ctg acc gcc ctg     1123
Ala Ile Thr Leu Asn Thr Ser Ser Gly Val Thr Gly Leu Thr Ala Leu
                330                 335                 340 aac acc aac acc agc ggc gcg gct caa acc gtc acc gcc ggc gct ggc     1171
Asn Thr Asn Thr Ser Gly Ala Ala Gln Thr Val Thr Ala Gly Ala Gly
            345                 350                 355 cag aac ctg acc gcc acg acc gcc gct caa gcc gcg aac aac gtc gcc     1219
Gln Asn Leu Thr Ala Thr Thr Ala Ala Gln Ala Ala Asn Asn Val Ala
        360                 365                 370 gtc gac ggg cgc gcc aac gtc acc gtc gcc tcg acg ggc gtg acc tcg     1267
Val Asp Gly Arg Ala Asn Val Thr Val Ala Ser Thr Gly Val Thr Ser
375                 380                 385 ggc acg acc acg gtc ggc gcc aac tcg gcc gct tcg ggc acc gtg tcg     1315
Gly Thr Thr Thr Val Gly Ala Asn Ser Ala Ala Ser Gly Thr Val Ser
390                 395                 400                 405 gtg agc gtc gcg aac tcg agc acg acc acg ggc gct atc gcc gtg         1363
Val Ser Val Ala Asn Ser Ser Thr Thr Thr Gly Ala Ile Ala Val
                410                 415                 420 acc ggt ggt acg gcc gtg acc gtg gct caa acg gcc ggc aac gcc gtg     1411
Thr Gly Gly Thr Ala Val Thr Val Ala Gln Thr Ala Gly Asn Ala Val
            425                 430                 435 aac acc acg ttg acg caa gcc gac gtg acc gtg acc ggt aac tcc agc     1459
Asn Thr Thr Leu Thr Gln Ala Asp Val Thr Val Thr Gly Asn Ser Ser
        440                 445                 450 acc acg gcc gtg acg gtc acc caa acc gcc gcc gcc acc gcc ggc gct     1507
Thr Thr Ala Val Thr Val Thr Gln Thr Ala Ala Ala Thr Ala Gly Ala
    455                 460                 465 acg gtc gcc ggt cgc gtc aac ggc gct gtg acg atc acc gac tct gcc     1555
Thr Val Ala Gly Arg Val Asn Gly Ala Val Thr Ile Thr Asp Ser Ala
470                 475                 480                 485 gcc gcc tcg gcc acg acc gcc ggc aag atc gcc acg gtc acc ctg ggc     1603
Ala Ala Ser Ala Thr Thr Ala Gly Lys Ile Ala Thr Val Thr Leu Gly
                490                 495                 500 agc ttc ggc gcc gcc acg atc gac tcg agc gct ctg acg acc gtc aac     1651
Ser Phe Gly Ala Ala Thr Ile Asp Ser Ser Ala Leu Thr Thr Val Asn
            505                 510                 515 ctg tcg ggc acg ggc acc tcg ctc ggc atc ggc cgc ggc gct ctg acc     1699
Leu Ser Gly Thr Gly Thr Ser Leu Gly Ile Gly Arg Gly Ala Leu Thr
        520                 525                 530 gcc acg ccg acc gcc aac acc ctg acc ctg aac gtc aat ggt ctg acg     1747
Ala Thr Pro Thr Ala Asn Thr Leu Thr Leu Asn Val Asn Gly Leu Thr
    535                 540                 545 acg acc ggc gcg atc acg gac tcg gaa gcg gct gct gac gat ggt ttc     1795
Thr Thr Gly Ala Ile Thr Asp Ser Glu Ala Ala Ala Asp Asp Gly Phe
550                 555                 560                 565 acc acc atc aac atc gct ggt tcg acc gcc tct tcg acg atc gcc agc     1843
Thr Thr Ile Asn Ile Ala Gly Ser Thr Ala Ser Ser Thr Ile Ala Ser
                570                 575                 580 ctg gtg gcc gcc gac gcg acg acc ctg aac atc tcg ggc gac gct cgc     1891
```

```
Leu Val Ala Ala Asp Ala Thr Thr Leu Asn Ile Ser Gly Asp Ala Arg
            585                 590                 595 gtc acg atc acc tcg cac acc gct gcc gcc ctg acg ggc atc acg gtg      1939
Val Thr Ile Thr Ser His Thr Ala Ala Ala Leu Thr Gly Ile Thr Val
        600                 605                 610 acc aac agc gtt ggt gcg acc ctc ggc gcc gaa ctg gcg acc ggt ctg      1987
Thr Asn Ser Val Gly Ala Thr Leu Gly Ala Glu Leu Ala Thr Gly Leu
        615                 620                 625 gtc ttc acg ggc ggc gct ggc cgt gac tcg atc ctg ctg ggc gcc acg      2035
Val Phe Thr Gly Gly Ala Gly Arg Asp Ser Ile Leu Leu Gly Ala Thr
630                 635                 640                 645 acc aag gcg atc gtc atg ggc gcc ggc gac gac acc gtc acc gtc agc      2083
Thr Lys Ala Ile Val Met Gly Ala Gly Asp Asp Thr Val Thr Val Ser
                650                 655                 660 tcg gcg acc ctg ggc gct ggt ggt tcg gtc aac ggc ggc gac ggc acc      2131
Ser Ala Thr Leu Gly Ala Gly Gly Ser Val Asn Gly Gly Asp Gly Thr
            665                 670                 675 gac gtt ctg gtg gcc aac gtc aac ggt tcg tcg ttc agc gct gac ccg      2179
Asp Val Leu Val Ala Asn Val Asn Gly Ser Ser Phe Ser Ala Asp Pro
        680                 685                 690 gcc ttc ggc ggc ttc gaa acc ctc cgc gtc gct ggc gcg gcg gct caa      2227
Ala Phe Gly Gly Phe Glu Thr Leu Arg Val Ala Gly Ala Ala Ala Gln
        695                 700                 705 ggc tcg cac aac gcc aac ggc ttc acg gct ctg caa ctg ggc gcg acg      2275
Gly Ser His Asn Ala Asn Gly Phe Thr Ala Leu Gln Leu Gly Ala Thr
710                 715                 720                 725 gcg ggt gcg acg acc ttc acc aac gtt gcg gtg aat gtc ggc ctg acc      2323
Ala Gly Ala Thr Thr Phe Thr Asn Val Ala Val Asn Val Gly Leu Thr
                730                 735                 740 gtt ctg gcg gct ccg acc ggt acg acc gtg acc ctg gcc aac gcc          2371
Val Leu Ala Ala Pro Thr Gly Thr Thr Val Thr Leu Ala Asn Ala
            745                 750                 755 acg ggc acc tcg gac gtg ttc aac ctg acc ctg tcg tcc tcg gcc gct      2419
Thr Gly Thr Ser Asp Val Phe Asn Leu Thr Leu Ser Ser Ser Ala Ala
        760                 765                 770 ctg gcc gct ggt acg gtt gcg ctg gct ggc gtc gag acg gtg aac atc      2467
Leu Ala Ala Gly Thr Val Ala Leu Ala Gly Val Glu Thr Val Asn Ile
775                 780                 785 gcc gcc acc gac acc aac acg acc gct cac gtc gac acg ctg acg ctg      2515
Ala Ala Thr Asp Thr Asn Thr Thr Ala His Val Asp Thr Leu Thr Leu
790                 795                 800                 805 caa gcc acc tcg gcc aag tcg atc gtg gtg acg ggc aac gcc ggt ctg      2563
Gln Ala Thr Ser Ala Lys Ser Ile Val Val Thr Gly Asn Ala Gly Leu
                810                 815                 820 aac ctg acc aac acc ggc aac acg gct gtc acc agc ttc gac gcc agc      2611
Asn Leu Thr Asn Thr Gly Asn Thr Ala Val Thr Ser Phe Asp Ala Ser
            825                 830                 835 gcc gtc acc ggc acg gct ccg gct gtg acc ttc gtg tcg gcc aac acc      2659
Ala Val Thr Gly Thr Ala Pro Ala Val Thr Phe Val Ser Ala Asn Thr
        840                 845                 850 acg gtg ggt gaa gtc gtc acg atc cgc ggc ggc gct ggc gcc gac tcg      2707
Thr Val Gly Glu Val Val Thr Ile Arg Gly Gly Ala Gly Ala Asp Ser
855                 860                 865 ctg acc ggt tcg gcc acc gcc aat gac acc atc atc ggt ggc gct ggc      2755
Leu Thr Gly Ser Ala Thr Ala Asn Asp Thr Ile Ile Gly Gly Ala Gly
870                 875                 880                 885 gct gac acc ctg gtc tac acc ggc ggt acg gac acc ttc acg ggt ggc      2803
Ala Asp Thr Leu Val Tyr Thr Gly Gly Thr Asp Thr Phe Thr Gly Gly
            890                 895                 900
```

```
acg ggc gcg gat atc ttc gat atc aac gct atc ggc acc tcg acc gct    2851
Thr Gly Ala Asp Ile Phe Asp Ile Asn Ala Ile Gly Thr Ser Thr Ala
            905                 910                 915 ttc gtg acg atc acc gac gcc gct gtc ggc gac aag ctc gac ctc gtc    2899
Phe Val Thr Ile Thr Asp Ala Ala Val Gly Asp Lys Leu Asp Leu Val
        920                 925                 930 ggc atc tcg acg aac ggc gct atc gct gac ggc gcc ttc ggc gct gcg    2947
Gly Ile Ser Thr Asn Gly Ala Ile Ala Asp Gly Ala Phe Gly Ala Ala
935                 940                 945 gtc acc ctg ggc gct gct gcg acc ctg gct cag tac ctg gac gct gct    2995
Val Thr Leu Gly Ala Ala Ala Thr Leu Ala Gln Tyr Leu Asp Ala Ala
950                 955                 960                 965 gct gcc ggc gac ggc agc ggc acc tcg gtt gcc aag tgg ttc cag ttc    3043
Ala Ala Gly Asp Gly Ser Gly Thr Ser Val Ala Lys Trp Phe Gln Phe
            970                 975                 980 ggc ggc gac acc tat gtc gtc gtt gac agc tcg gct ggc gcg acc ttc    3091
Gly Gly Asp Thr Tyr Val Val Val Asp Ser Ser Ala Gly Ala Thr Phe
        985                 990                 995 gtc agc ggc gct gac gcg gtg atc aag ctg acc ggt ctg gtc acg ctg    3139
Val Ser Gly Ala Asp Ala Val Ile Lys Leu Thr Gly Leu Val Thr Leu
    1000                1005                1010 acc acc tcg gcc ttc gcc acc gaa gtc ctg acg ctc gcc taagcgaacg    3188
Thr Thr Ser Ala Phe Ala Thr Glu Val Leu Thr Leu Ala
1015                1020                1025 tctgatcctc gcctaggcga ggatcgctag actaagagac cccgtcttcc gaaagggagg    3248
cggggtcttt cttatgggcg ctacgcgctg gccggccttg cctagttccg gt          3300

<210> SEQ ID NO 7
<211> LENGTH: 1026
<212> TYPE: PRT
<213> ORGANISM: Caulobacter crescentus

<400> SEQUENCE: 7

Met Ala Tyr Thr Thr Ala Gln Leu Val Thr Ala Tyr Thr Asn Ala Asn
1               5                   10                  15

Leu Gly Lys Ala Pro Asp Ala Ala Thr Thr Leu Thr Leu Asp Ala Tyr
            20                  25                  30

Ala Thr Gln Thr Gln Thr Gly Gly Leu Ser Asp Ala Ala Ala Leu Thr
        35                  40                  45

Asn Thr Leu Lys Leu Val Asn Ser Thr Thr Ala Val Ala Ile Gln Thr
    50                  55                  60

Tyr Gln Phe Phe Thr Gly Val Ala Pro Ser Ala Ala Gly Leu Asp Phe
65                  70                  75                  80

Leu Val Asp Ser Thr Thr Asn Thr Asn Asp Leu Asn Asp Ala Tyr Tyr
                85                  90                  95

Ser Lys Phe Ala Gln Glu Asn Arg Phe Ile Asn Phe Ser Ile Asn Leu
            100                 105                 110

Ala Thr Gly Ala Gly Ala Gly Ala Thr Ala Phe Ala Ala Ala Tyr Thr
        115                 120                 125

Gly Val Ser Tyr Ala Gln Thr Val Ala Thr Ala Tyr Asp Lys Ile Ile
    130                 135                 140

Gly Asn Ala Val Ala Thr Ala Ala Gly Val Asp Val Ala Ala Val
145                 150                 155                 160

Ala Phe Leu Ser Arg Gln Ala Asn Ile Asp Tyr Leu Thr Ala Phe Val
                165                 170                 175

Arg Ala Asn Thr Pro Phe Thr Ala Ala Ala Asp Ile Asp Leu Ala Val
            180                 185                 190
```

```
Lys Ala Ala Leu Ile Gly Thr Ile Leu Asn Ala Ala Thr Val Ser Gly
            195                 200                 205

Ile Gly Gly Tyr Ala Thr Ala Thr Ala Ala Met Ile Asn Asp Leu Ser
        210                 215                 220

Asp Gly Ala Leu Ser Thr Asp Asn Ala Ala Gly Val Asn Leu Phe Thr
225                 230                 235                 240

Ala Tyr Pro Ser Ser Gly Val Ser Gly Ser Thr Leu Ser Leu Thr Thr
                245                 250                 255

Gly Thr Asp Thr Leu Thr Gly Thr Ala Asn Asn Asp Thr Phe Val Ala
            260                 265                 270

Gly Glu Val Ala Gly Ala Ala Thr Leu Thr Val Gly Asp Thr Leu Ser
        275                 280                 285

Gly Gly Ala Gly Thr Asp Val Leu Asn Trp Val Gln Ala Ala Ala Val
290                 295                 300

Thr Ala Leu Pro Thr Gly Val Thr Ile Ser Gly Ile Glu Thr Met Asn
305                 310                 315                 320

Val Thr Ser Gly Ala Ala Ile Thr Leu Asn Thr Ser Ser Gly Val Thr
                325                 330                 335

Gly Leu Thr Ala Leu Asn Thr Asn Thr Ser Gly Ala Ala Gln Thr Val
            340                 345                 350

Thr Ala Gly Ala Gly Gln Asn Leu Thr Ala Thr Thr Ala Ala Gln Ala
        355                 360                 365

Ala Asn Asn Val Ala Val Asp Gly Arg Ala Asn Val Thr Val Ala Ser
370                 375                 380

Thr Gly Val Thr Ser Gly Thr Thr Val Gly Ala Asn Ser Ala Ala
385                 390                 395                 400

Ser Gly Thr Val Ser Val Ser Val Ala Asn Ser Ser Thr Thr Thr Thr
                405                 410                 415

Gly Ala Ile Ala Val Thr Gly Gly Thr Ala Val Thr Val Ala Gln Thr
            420                 425                 430

Ala Gly Asn Ala Val Asn Thr Thr Leu Thr Gln Ala Asp Val Thr Val
        435                 440                 445

Thr Gly Asn Ser Ser Thr Thr Ala Val Thr Val Thr Gln Thr Ala Ala
450                 455                 460

Ala Thr Ala Gly Ala Thr Val Ala Gly Arg Val Asn Gly Ala Val Thr
465                 470                 475                 480

Ile Thr Asp Ser Ala Ala Ala Ser Ala Thr Thr Ala Gly Lys Ile Ala
                485                 490                 495

Thr Val Thr Leu Gly Ser Phe Gly Ala Ala Thr Ile Asp Ser Ser Ala
            500                 505                 510

Leu Thr Thr Val Asn Leu Ser Gly Thr Gly Thr Ser Leu Gly Ile Gly
        515                 520                 525

Arg Gly Ala Leu Thr Ala Thr Pro Thr Ala Asn Thr Leu Thr Leu Asn
530                 535                 540

Val Asn Gly Leu Thr Thr Thr Gly Ala Ile Thr Asp Ser Glu Ala Ala
545                 550                 555                 560

Ala Asp Asp Gly Phe Thr Thr Ile Asn Ile Ala Gly Ser Thr Ala Ser
                565                 570                 575

Ser Thr Ile Ala Ser Leu Val Ala Ala Asp Ala Thr Thr Leu Asn Ile
            580                 585                 590

Ser Gly Asp Ala Arg Val Thr Ile Thr Ser His Thr Ala Ala Ala Leu
        595                 600                 605
```

```
Thr Gly Ile Thr Val Thr Asn Ser Val Gly Ala Thr Leu Gly Ala Glu
        610                 615                 620

Leu Ala Thr Gly Leu Val Phe Thr Gly Gly Ala Gly Arg Asp Ser Ile
625                 630                 635                 640

Leu Leu Gly Ala Thr Thr Lys Ala Ile Val Met Gly Ala Gly Asp Asp
                645                 650                 655

Thr Val Thr Val Ser Ser Ala Thr Leu Gly Ala Gly Gly Ser Val Asn
                660                 665                 670

Gly Gly Asp Gly Thr Asp Val Leu Val Ala Asn Val Asn Gly Ser Ser
                675                 680                 685

Phe Ser Ala Asp Pro Ala Phe Gly Gly Phe Glu Thr Leu Arg Val Ala
690                 695                 700

Gly Ala Ala Ala Gln Gly Ser His Asn Ala Asn Gly Phe Thr Ala Leu
705                 710                 715                 720

Gln Leu Gly Ala Thr Ala Gly Ala Thr Thr Phe Thr Asn Val Ala Val
                725                 730                 735

Asn Val Gly Leu Thr Val Leu Ala Ala Pro Thr Gly Thr Thr Thr Val
                740                 745                 750

Thr Leu Ala Asn Ala Thr Gly Thr Ser Asp Val Phe Asn Leu Thr Leu
        755                 760                 765

Ser Ser Ser Ala Ala Leu Ala Ala Gly Thr Val Ala Leu Ala Gly Val
        770                 775                 780

Glu Thr Val Asn Ile Ala Ala Thr Asp Thr Asn Thr Thr Ala His Val
785                 790                 795                 800

Asp Thr Leu Thr Leu Gln Ala Thr Ser Ala Lys Ser Ile Val Val Thr
                805                 810                 815

Gly Asn Ala Gly Leu Asn Leu Thr Asn Thr Gly Asn Thr Ala Val Thr
                820                 825                 830

Ser Phe Asp Ala Ser Ala Val Thr Gly Thr Ala Pro Ala Val Thr Phe
        835                 840                 845

Val Ser Ala Asn Thr Thr Val Gly Glu Val Val Thr Ile Arg Gly Gly
850                 855                 860

Ala Gly Ala Asp Ser Leu Thr Gly Ser Ala Thr Ala Asn Asp Thr Ile
865                 870                 875                 880

Ile Gly Gly Ala Gly Ala Asp Thr Leu Val Tyr Thr Gly Gly Thr Asp
                885                 890                 895

Thr Phe Thr Gly Gly Thr Gly Ala Asp Ile Phe Asp Ile Asn Ala Ile
                900                 905                 910

Gly Thr Ser Thr Ala Phe Val Thr Ile Thr Asp Ala Ala Val Gly Asp
        915                 920                 925

Lys Leu Asp Leu Val Gly Ile Ser Thr Asn Gly Ala Ile Ala Asp Gly
        930                 935                 940

Ala Phe Gly Ala Ala Val Thr Leu Gly Ala Ala Ala Thr Leu Ala Gln
945                 950                 955                 960

Tyr Leu Asp Ala Ala Ala Gly Asp Gly Ser Gly Thr Ser Val Ala
                965                 970                 975

Lys Trp Phe Gln Phe Gly Gly Asp Thr Tyr Val Val Asp Ser Ser
                980                 985                 990

Ala Gly Ala Thr Phe Val Ser Gly Ala Asp Ala Val Ile Lys Leu Thr
        995                 1000                1005

Gly Leu Val Thr Leu Thr Thr Ser Ala Phe Ala Thr Glu Val Leu Thr
        1010                1015                1020

Leu Ala
```

-continued

1025

<210> SEQ ID NO 8
<211> LENGTH: 17
<212> TYPE: PRT
<213> ORGANISM: Pseudomonas aeroginosa
<220> FEATURE:
<221> NAME/KEY: VARIANT
<222> LOCATION: (1)...(17)
<223> OTHER INFORMATION: Xaa = Any Amino Acid

<400> SEQUENCE: 8

Xaa Cys Thr Ser Asp Gln Asp Glu Gln Phe Ile Pro Lys Gly Cys Ser
 1               5                  10                  15

Xaa

<210> SEQ ID NO 9
<211> LENGTH: 184
<212> TYPE: PRT
<213> ORGANISM: Infectious Hematopoietic Nervosis Virus

<400> SEQUENCE: 9

Glu Tyr Asn Ser Gly Ala Glu Ile Leu Ser Phe Pro Lys Cys Glu Asp
 1               5                  10                  15

Lys Thr Met Gly Met Arg Gly Asn Leu Asp Asp Phe Ala Tyr Leu Asp
             20                  25                  30

Asp Leu Val Lys Ala Ser Glu Ser Arg Glu Glu Cys Leu Glu Ala His
         35                  40                  45

Ala Glu Ile Ile Ser Thr Asn Ser Val Thr Pro Tyr Leu Leu Ser Lys
     50                  55                  60

Phe Arg Ser Pro His Pro Gly Ile Asn Asp Val Tyr Ala Met His Lys
 65                  70                  75                  80

Gly Ser Ile Tyr His Gly Met Ser Met Thr Val Ala Val Asp Glu Val
                 85                  90                  95

Ser Lys Asp Arg Thr Thr Tyr Arg Ala His Arg Ala Thr Ser Phe Thr
            100                 105                 110

Lys Trp Glu Arg Pro Phe Gly Asp Glu Trp Glu Gly Phe His Gly Leu
        115                 120                 125

His Gly Asn Asn Thr Thr Ile Ile Pro Asp Leu Glu Lys Tyr Val Ala
    130                 135                 140

Gln Tyr Lys Thr Ser Met Met Glu Pro Met Ser Ile Lys Ser Val Pro
145                 150                 155                 160

His Pro Ser Ile Leu Ala Phe Tyr Asn Glu Thr Asp Leu Ser Gly Ile
                165                 170                 175

Ser Ile Arg Lys Leu Asp Ser Phe
            180

<210> SEQ ID NO 10
<211> LENGTH: 12
<212> TYPE: DNA
<213> ORGANISM: Artificial Sequence
<220> FEATURE:
<223> OTHER INFORMATION: Synthetically generated linker

<400> SEQUENCE: 10
cgacggatcc gt                                                        12

<210> SEQ ID NO 11
<211> LENGTH: 17
<212> TYPE: PRT

```
<213> ORGANISM: Artificial Sequence
<220> FEATURE:
<223> OTHER INFORMATION: Synthetically generated peptide

<400> SEQUENCE: 11

Ala Glu Ala Ala Ala Lys Glu Ala Ala Lys Cys Ala Ala Ala His
 1               5                  10                  15
Ala

<210> SEQ ID NO 12
<211> LENGTH: 552
<212> TYPE: DNA
<213> ORGANISM: Infectious Hematopoietic Nervosis Virus
<220> FEATURE:
<221> NAME/KEY: CDS
<222> LOCATION: (1)...(552)

<400> SEQUENCE: 12 gaa tac aat tct gga gca gaa atc ctc tcg ttc ccg aag tgt gag gac    48
Glu Tyr Asn Ser Gly Ala Glu Ile Leu Ser Phe Pro Lys Cys Glu Asp
 1               5                  10                  15 aag acg atg ggg atg agg gga aac ttg gat gac ttt gcc tat cta gac    96
Lys Thr Met Gly Met Arg Gly Asn Leu Asp Asp Phe Ala Tyr Leu Asp
             20                  25                  30 gat ctg gtg aag gcc tct gag agc aga gag gaa tgt ctt gag gcg cac   144
Asp Leu Val Lys Ala Ser Glu Ser Arg Glu Glu Cys Leu Glu Ala His
         35                  40                  45 gcc gag ata ata tca aca aac agt gtg act cca tac ctc cta tcc aag   192
Ala Glu Ile Ile Ser Thr Asn Ser Val Thr Pro Tyr Leu Leu Ser Lys
     50                  55                  60 ttc cga tct cca cat ccc gga ata aat gac gtc tac gct atg cac aaa   240
Phe Arg Ser Pro His Pro Gly Ile Asn Asp Val Tyr Ala Met His Lys
 65                  70                  75                  80 ggc tcc atc tat cac ggg atg tcc atg acg gtc gct gtg gac gag gta   288
Gly Ser Ile Tyr His Gly Met Ser Met Thr Val Ala Val Asp Glu Val
                 85                  90                  95 tcc aag gac agg acg acg tac agg gcc cat cgc gct acc agc ttc acg   336
Ser Lys Asp Arg Thr Thr Tyr Arg Ala His Arg Ala Thr Ser Phe Thr
            100                 105                 110 aaa tgg gaa cga ccc ttt ggg gat gag tgg gag ggc ttt cac gga ttg   384
Lys Trp Glu Arg Pro Phe Gly Asp Glu Trp Glu Gly Phe His Gly Leu
        115                 120                 125 cac gga aac aac acc acc att att cca gac ctg gag aaa tac gtc gcc   432
His Gly Asn Asn Thr Thr Ile Ile Pro Asp Leu Glu Lys Tyr Val Ala
    130                 135                 140 cag tac aag acg agc atg atg gaa ccg atg agc atc aaa tcc gta ccc   480
Gln Tyr Lys Thr Ser Met Met Glu Pro Met Ser Ile Lys Ser Val Pro
145                 150                 155                 160 cat cca agc atc ctg gcc ttc tac aat gag aca gac tta tca ggg atc   528
His Pro Ser Ile Leu Ala Phe Tyr Asn Glu Thr Asp Leu Ser Gly Ile
                165                 170                 175 tcc atc agg aaa ttg gac tca ttc                                    552
Ser Ile Arg Lys Leu Asp Ser Phe
            180
```